United States Patent
Wada

(10) Patent No.: US 10,365,274 B2
(45) Date of Patent: Jul. 30, 2019

(54) IMMUNOCHROMATOGRAPHIC KIT

(71) Applicant: FUJIFILM Corporation, Tokyo (JP)

(72) Inventor: Atsuhiko Wada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 204 days.

(21) Appl. No.: 15/649,009

(22) Filed: Jul. 13, 2017

(65) Prior Publication Data

US 2017/0307603 A1   Oct. 26, 2017

Related U.S. Application Data

(63) Continuation of application No. PCT/JP2016/000086, filed on Jan. 8, 2016.

(30) Foreign Application Priority Data

Jan. 16, 2015   (JP) .................................. 2015-006525
Mar. 26, 2015   (JP) .................................. 2015-064392

(51) Int. Cl.
   *G01N 33/543*   (2006.01)
   *G01N 33/558*   (2006.01)

(52) U.S. Cl.
   CPC ............................ *G01N 33/54386* (2013.01);
       *01N 33/54366* (2013.01); *G01N 33/558* (2013.01)

(58) Field of Classification Search
   CPC ............ G01N 33/54386; G01N 33/558; G01N 33/54366; C12Q 1/6883; C12Q 1/3827;
   (Continued)

(56) References Cited

U.S. PATENT DOCUMENTS 5,173,261 A   12/1992   Krause et al.
6,017,494 A *   1/2000   Ashihara ............... B01L 3/5023
                                                  422/412

(Continued)

FOREIGN PATENT DOCUMENTS

JP   4-225146 A   8/1992
JP   2009-85700 A   4/2009

(Continued)

OTHER PUBLICATIONS

International Search Report, issued in PCT/JP2016/000086, PCT/ISA/210, dated Apr. 26, 2016.

(Continued)

*Primary Examiner* — Michael L Hobbs
(74) *Attorney, Agent, or Firm* — Birch, Stewart, Kolasch & Birch, LLP

(57) ABSTRACT

The immunochromatographic kit includes an inspection strip which includes an insoluble carrier spreading the specimen liquid, a label-holding pad including a label substance modified with a first substance bondable to a test substance, a liquid-sending pad sending a first amplification liquid to the insoluble carrier, and an absorption pad disposed in contact with the other end of the insoluble carrier and sequentially has an inspection region including a second substance being bonded to the test substance, a confirmation region including a substance bondable to the first substance, and an amplification index region including a substance being reacted with the first amplification liquid between the label-holding pad and the absorption pad of the insoluble carrier, a first pot being disposed below the liquid-sending pad and enclosing the first amplification liquid, and a second pot being disposed above the absorption pad and enclosing a second amplification liquid in a housing case.

22 Claims, 7 Drawing Sheets

(58) Field of Classification Search
CPC .............. C12Q 1/6816; C12Q 1/6869; C12Q 2600/156
See application file for complete search history.

(56) References Cited

U.S. PATENT DOCUMENTS

| | | | | |
|---|---|---|---|---|
| 2012/0058465 | A1* | 3/2012 | Mori | G01N 33/54386 435/5 |
| 2013/0084580 | A1 | 4/2013 | Wada et al. | |
| 2016/0025752 | A1* | 1/2016 | Santiago | G01N 21/8483 436/501 |
| 2018/0292398 | A1* | 10/2018 | Wada | G01N 33/543 |

FOREIGN PATENT DOCUMENTS

| | | |
|---|---|---|
| JP | 2010-230634 A | 10/2010 |
| JP | 2011-99724 A | 5/2011 |
| JP | 2012-103150 A | 5/2012 |
| JP | 2013-213803 A | 10/2013 |
| JP | 2014-66674 A | 4/2014 |

OTHER PUBLICATIONS

Written Opinion of the International Searching Authority, issued in PCT/JP2016/000086, PCT/ISA/237, dated Apr. 26, 2016.

International Preliminary Report on Patentability (Form PCT/IPEA/409), dated Dec. 27, 2016, for International Application No. PCT/JP2016/000086, along with an English translation.

Extended European Search Report, dated Nov. 7, 2017, for European Application No. 16737193.9.

Mori et al., "Development of Highly Sensitive Immunochromatographic Detection Kit for Seasonal Influenza Virus Using Silver Amplification," Fujifilm Research & Development, No. 57, Feb. 27, 2012, XP055198514, pp. 5-11 (Total pages 7).

* cited by examiner

IMMUNOCHROMATOGRAPHIC KIT

CROSS-REFERENCE TO RELATED APPLICATIONS

This application is a continuation application of International Application No. PCT/JP2016/000086 filed Jan. 8, 2016, which claims priority under 35 U.S.C. § 119(a) to Japanese Patent Application No. 2015-006525, filed Jan. 16, 2015, and Japanese Patent Application No. 2015-064392, filed Mar. 26, 2015. Each of the above applications is hereby expressly incorporated by reference, in its entirety, into the present application.

BACKGROUND OF THE INVENTION

1. Field of the Invention

The present invention relates to an immunochromatographic kit used to carry out signal amplification operation for enhancing detection sensitivity.

2. Description of the Related Art

Among immunoassay methods, immunochromatography is easy to operate and is capable of finishing measurement within a short period of time and is thus, generally, widely used as a simple method for detecting test substances.

In immunochromatography, in order to avoid a problem of false negative in which test substances are not detected due to poor sensitivity even when being included, techniques for amplifying detection signals are being proposed. As methods for amplifying detection signals, methods in which two kinds of liquid, one for catalyzing amplification and the other for carrying out amplification, are used are known. Particularly, a method for amplifying by causing a solution including silver ions and a solution including a silver ion reducing agent to react with labels made of metal colloids, metal sulfides, or the like is promising as techniques for easily measuring the amount of test substances at a high sensitivity. Immunochromatography in which the above-described amplification is used are described in JP2011-99724A, JP2012-103150A, JP2013-213803A, JP2014-066674A, and the like.

In the above-described method for amplifying detection signals, it is necessary to control supply timing of two kinds of liquid, one for catalyzing amplification such as solutions including silver ion reducing agents and the other for carrying out amplification such as solutions including silver ions, methods for supplying the liquid, and supply locations. When the flow direction of liquid or the supply timing of liquid remains undetermined, amplification reactions cannot be normally caused or background signals are intensified, and thus there are cases in which substances being tests cannot be appropriately detected. Therefore, in order to accurately control the timing, methods, and locations for supplying two kinds of liquid, it is preferable to control measurement using exclusive devices from the viewpoint of ensuring accuracy such as repetitive reproducibility.

In JP2011-99724A, a method in which the spread direction of liquid carrying out amplification is set to be 90° with respect to the spread direction of solutions being tested is employed, but there is no detailed description on the supply timing of liquid. On the other hand, JP2012-103150A discloses an exclusive analyzer enabling highly sensitive detection by determining the supply timing of liquid.

SUMMARY OF THE INVENTION

However, the analyzer as described in JP2012-103150A cannot be used in the status of electricity infrastructures not properly working such as disasters or in the environment with no electricity supply. Therefore, even when highly sensitive measurement is made using amplification techniques for which a plurality of liquids are used in the above-described emergency situations or in the environment with no analyzers installed, there is a problem in that favorable repetitive reproducibility or highly accurate measurement cannot be realized.

In order to amplify signals, there are cases in which portions on an immunochromatographic carrier which need to be amplified are amplified by being immersed in a first liquid out of the above-described two liquids and then supplying a second liquid. In order to prevent the occurrence of poor amplification due to the mismatch of the supply timing of the second liquid, JP2013-213803A discloses a chromatographic kit to which a region for detecting the first liquid is provided so that portions on a chromatographic carrier which need to be amplified being immersed in the first liquid can be easily confirmed.

In addition, JP2014-066674A discloses a method enabling normal amplification reactions by determining the addition of specimens being tested to chromatographic carriers and the addition timing of the first liquid in chromatographic kits having the same constitution as in JP2013-213803A.

Meanwhile, the chromatographic kits described in JP2013-213803A and JP2014-066674A are constituted so that the first and second liquids for signal amplification are injected through filling holes provided in a housing case which includes a chromatographic carrier of the chromatographic kit, and the first and second liquids are not integrally constituted in the housing case.

However, as an immunochromatographic kit, when at least liquid for amplification is not integrally constituted with the kit as a chemical substance necessary for measurement, it is difficult to realize highly sensitive measurement in the case of disaster, in the status of a variety of infrastructures not property working, in the environment with no electricity supply, in the environment with no analyzers installed, and the like.

A first aspect of the present invention has been made in consideration of the above-described circumferences and aims to provide an immunochromatographic kit which realizes highly sensitive measurement for which an exclusive analyzer is not required.

In addition, in an immunochromatographic method for carrying out the above-described signal amplification, it is necessary to supply specimen liquid and two kinds of liquid for amplification to an immunochromatographic carrier, and the amount of liquid to be supplied is greater compared with the case of measurement methods in which amplification is not carried out. Therefore, depending on the length of immunochromatographic strips or the water absorption force of pads absorbing liquid (absorption pads), there is a problem in that the inspection time becomes unreasonably long. In the point of care testing (POCT) in which measurement is carried out at medical examination sites such as hospitals, the inspection time becoming long is not desirable.

A second aspect of the present invention has been made in consideration of the above-described circumstances and aims to provide an immunochromatographic kit which realizes highly sensitive measurement for which an exclusive analyzer is not required within an appropriate inspection time.

The immunochromatographic kit of the first aspect of the present invention is an immunochromatographic kit detecting a test substance in a specimen liquid, comprising: an inspection strip that includes an insoluble carrier spreading the specimen liquid, a label-holding pad including a label substance modified with a first substance bondable to the test substance fixed on the insoluble carrier, a liquid-sending pad in contact with one end of the insoluble carrier and sending a first amplification liquid to the insoluble carrier, and an absorption pad in contact with another end of the insoluble carrier, and the inspection strip sequentially having an inspection region including a second substance bonded to the test substance, a confirmation region including a substance bondable to the first substance, and an amplification index region including a substance that reacts with the first amplification liquid, from a label-holding pad side between the label-holding pad and the absorption pad of the insoluble carrier; a first pot disposed below the liquid-sending pad and enclosing the first amplification liquid; a second pot disposed above the absorption pad and enclosing a second amplification liquid; and a housing case containing the inspection strip, the first pot, and the second pot and having a pore for dropwise addition of the specimen liquid facing the label-holding pad.

Meanwhile, here, the second amplification liquid is liquid different from the first amplification liquid and acts on the label substance together with the first amplification liquid so as to exhibit an effect of amplifying signals from a label.

In the immunochromatographic kit of the first aspect of the present invention, it is preferable that the housing case includes an upper case having the pore for dropwise addition of the specimen liquid, a lower case having an accommodation portion in which the inspection strip is disposed, and a middle member disposed between the upper case and the lower case and the middle member has a pot accommodation portion that accommodates the second pot and includes a hole for causing the second amplification liquid to flow down, in a bottom surface thereof.

In the above description, it is desirable that each of the first pot and the second pot has one surface including a sheet member. Here, the sheet member is made of a sheet that can be broken by an external pressing action.

At this time, it is preferable that a protrusion portion breaking the sheet member of the second pot is provided in the pot accommodation portion of the middle member against the sheet member of the second pot and, the immunochromatographic kit is provided with a movable member relatively moving the second pot with respect to the protrusion portion to a location at which the sheet member is broken by the protrusion portion.

Here, "being relatively moved" means that the second pot may be moved toward the protrusion portion, the protrusion portion may be moved toward the second pot, or furthermore, both the second pot and the protrusion portion are moved toward each other.

In the immunochromatographic kit of the first aspect of the present invention, it is preferable that the surface including the sheet member of the first pot is disposed against the liquid-sending pad and a movable member is disposed at a location facing the sheet member of the first pot through the liquid-sending pad and presses and displaces the liquid-sending pad in response to an external pressing force to break the sheet member of the first pot and press the liquid-sending pad into the first pot.

In the immunochromatographic kit of the first aspect of the present invention, it is desirable that at least two sides of the label-holding pad are covered with a film-like fixation member and are fixed to the insoluble carrier and a region of the label-holding pad facing the pore for dropwise addition of the specimen liquid of the housing case is not covered with the film-like fixation member.

In the immunochromatographic kit of the first aspect of the present invention, it is preferable that a reducing agent liquid for silver ions is used as the first amplification liquid and a solution including silver ions is used as the second amplification liquid.

Here, it is particularly preferable that the first amplification liquid is a solution including divalent iron ions.

In the immunochromatographic kit of the first aspect of the present invention, it is preferable that a substance which is included in the amplification index region and is reacted with the first amplification liquid is a substance being reacted through protons.

In addition, it is preferable that the label substance modified with the first substance bondable to the test substance fixed on the insoluble carrier which is included in the label-holding pad is a metal colloid.

An immunochromatographic kit of a second aspect of the present invention is an immunochromatographic kit detecting a test substance in a specimen liquid, comprising: an inspection strip that includes an insoluble carrier spreading the specimen liquid, a label-holding pad including a label substance modified with a first substance bondable to the test substance fixed on the insoluble carrier, a liquid-sending pad in contact with one end of the insoluble carrier and sending a first amplification liquid to the insoluble carrier, and an absorption pad in contact with another end of the insoluble carrier, and the inspection strip having an inspection region including a second substance bonded to the test substance between the label-holding pad and the absorption pad of the insoluble carrier; a first pot disposed below the liquid-sending pad and enclosing the first amplification liquid; a second pot disposed above the absorption pad and enclosing a second amplification liquid; and a housing case containing the inspection strip, the first pot, and the second pot, in which the housing case comprises a lower case including an accommodation portion in which the inspection strip is disposed, an upper case fitted with the lower case, and a flow path-forming member disposed between the upper case and the lower case, the flow path-forming member has one surface forming a gap that guides the second amplification liquid, which is added dropwise onto the insoluble carrier onto the inspection region, between a surface of the insoluble carrier and the flow path-forming member, a water absorption force of the absorption pad is from 45 μL/minute to 90 μL/minute, and in a case in which, a liquid-sending pad side is designated as upstream and an absorption pad side is designated as downstream in the inspection strip, a distance between the one end of the insoluble carrier and an upstream-side end of the absorption pad is from 44 mm to 64 mm, and a distance between an upstream-side end of the surface of the flow path-forming member and a downstream-side end of the label-holding pad is from 1 mm to 19 mm.

Meanwhile, here, the second amplification liquid is liquid different from the first amplification liquid and acts on the label substance together with the first amplification liquid so as to exhibit an effect of amplifying signals from a label.

In the immunochromatographic kit of the second aspect of the present invention, it is preferable that the gap guiding the second amplification liquid onto the inspection region is from 0.01 mm to 1.00 mm.

In the immunochromatographic kit of the second aspect of the present invention, it is preferable that a distance between an upstream-side end of the label-holding pad and a downstream-side end of the liquid-sending pad is from 12 mm to 30 mm.

In the immunochromatographic kit of the second aspect of the present invention, it is preferable that a distance between the one end of the insoluble carrier and the upstream-side end of the absorption pad is from 49 mm to 59 mm.

In the immunochromatographic kit of the second aspect of the present invention, it is preferable that the water absorption force of the absorption pad is from 65 µL/minute to 75 µL/minute.

In the immunochromatographic kit of the second aspect of the present invention, it is preferable that a confirmation region including a substance bondable to the first substance and an amplification index region including a substance that reacts with the first amplification liquid are sequentially provided from an inspection region side between the inspection region on the insoluble carrier and the absorption pad.

It is preferable that a substance which is included in the amplification index region and is reacted with the first amplification liquid is a substance reacted through protons.

In the immunochromatographic kit of the second aspect of the present invention, it is preferable that the immunochromatographic kit is provided with a middle member disposed between the upper case and the lower case and the middle member has a pot accommodation portion that accommodates the second pot and includes a hole for adding the second amplification liquid dropwise onto the insoluble carrier in a bottom surface thereof.

Meanwhile, it is preferable that the middle member is integrally formed with the flow path-forming member.

The immunochromatographic kit of the second aspect of the present invention is preferably constituted so that the second amplification liquid is added dropwise on the downstream side of the inspection region in the insoluble carrier.

In the immunochromatographic kit of the second aspect of the present invention, it is preferable that a reducing agent liquid for silver ions is used as the first amplification liquid and a solution including silver ions is used as the second amplification liquid.

In the immunochromatographic kit of the second aspect of the present invention, it is preferable that a solution including divalent iron ions is used as the first amplification liquid.

In addition, it is preferable that the label substance modified with the first substance bondable to the test substance fixed on the insoluble carrier which is included in the label-holding pad is a metal colloid.

Since the immunochromatographic kit of the first aspect of the present invention includes the first pot enclosing the first amplification liquid for signal amplification and the second pot enclosing the second amplification liquid in the housing case together with the inspection strip, it is not necessary to separately prepare the first pot and the second pot in order to inject the first and second amplification liquids from the outside, and it is possible to carry out highly sensitive detection by means of signal amplification using only one immunochromatographic kit. In addition, since the amplification index region including the substance being reacted with the first amplification liquid is provided in the insoluble carrier, and the supply timing of the second amplification liquid can be visually recognized, it is possible to normally carry out amplification reactions without exclusive analyzers. Therefore, the immunochromatographic kit of the present invention is particularly useful in the case of emergency situations in which no exclusive analyzers are provided or analyzers are not available, disaster, and the like.

In addition, since the pot of the first amplification liquid is provided below the liquid-sending pad, regarding the sending of the first amplification liquid, it is possible to spread the first amplification liquid toward the label-holding pad side by immersing the liquid-sending pad in the first amplification liquid and thus permeating the first amplification liquid into the liquid-sending pad through the capillary action, and thus the first amplification liquid can be spread from the inside of the liquid-sending pad. Compared with a case in which amplification liquid is added dropwise from above the liquid-sending pad, it is possible to reliably permeate the first amplification liquid into the inside of the insoluble carrier and obtain a more favorable amplification effect.

Since the immunochromatographic kit of the second aspect of the present invention includes the first pot enclosing the first amplification liquid for signal amplification and the second pot enclosing the second amplification liquid in the housing case together with the inspection strip, it is not necessary to separately prepare the first pot and the second pot in order to inject the first and second amplification liquids from the outside, and it is possible to carry out highly sensitive detection by means of signal amplification using only one immunochromatographic kit. The immunochromatographic kit of the present invention is particularly useful in the case of emergency situations in which no exclusive analyzers are provided or analyzers are not available, disaster, and the like.

In addition, since the pot of the first amplification liquid is provided below the liquid-sending pad, regarding the sending of the first amplification liquid, it is possible to spread the first amplification liquid toward the label-holding pad side by immersing the liquid-sending pad in the first amplification liquid and thus permeating the first amplification liquid into the liquid-sending pad through the capillary action, and thus the first amplification liquid can be spread from the inside of the liquid-sending pad. Compared with a case in which amplification liquid is added dropwise from above the liquid-sending pad, it is possible to reliably permeate the first amplification liquid into the inside of the insoluble carrier and obtain a more favorable amplification effect.

Since the housing case includes the lower case including the accommodation portion in which the inspection strip is disposed, the upper case being fitted with the lower case, and the flow path-forming member being disposed between the upper case and the lower case, the flow path-forming member has the surface forming the gap that guides the second amplification liquid which is added dropwise onto the insoluble carrier onto the inspection region between the surface of the insoluble carrier and the flow path-forming member, the water absorption force of the absorption pad is from 45 µL/minute to 90 µL/minute, when the liquid-sending pad side is considered as upstream and the absorption pad side is considered as downstream in the inspection strip, the distance between one end of the insoluble carrier and the upstream-side end of the absorption pad is from 44 mm to 64 mm, and the distance between the upstream-side end of the surface of the flow path-forming member and the downstream-side end of the label-holding pad is from 1 mm to 19 mm, it is possible to realize inspection time suitable for POCT without excessively extending the inspection time.

DESCRIPTION OF THE PREFERRED EMBODIMENTS

Figure 1:
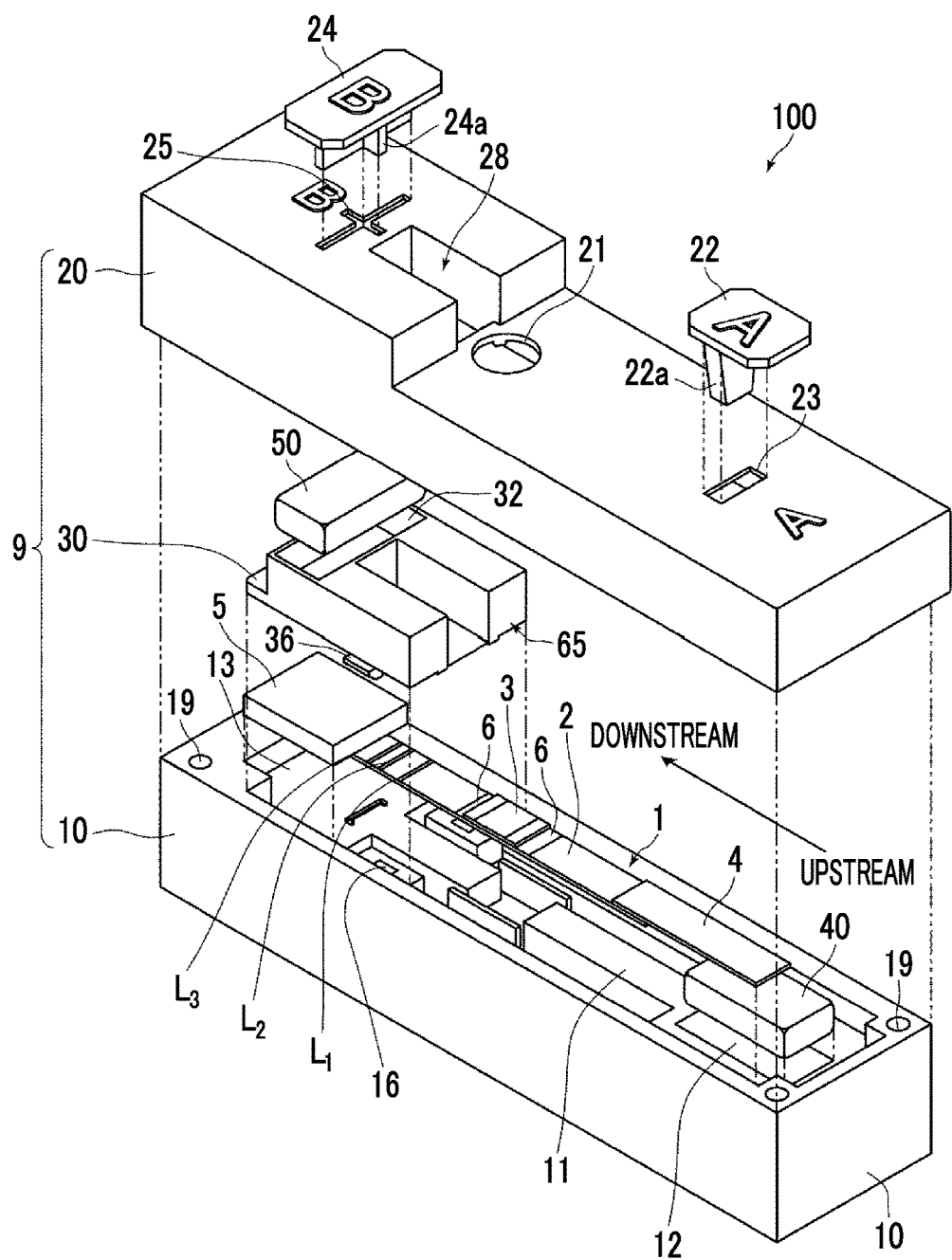
FIG. 1 is an exploded schematic perspective view illustrating an aspect of a first embodiment of an immunochromatographic kit of the present invention.

Hereinafter, an embodiment of the present invention will be described using the accompanying drawings, but the present invention is not limited thereto. Meanwhile, in order for better visibility, the reduction scales and the like of individual constitutional elements in the drawings are appropriately changed from actual sizes. Meanwhile, the present embodiment described below is an embodiment of the first aspect of the present invention and is also an embodiment of the second aspect of the present invention.

FIG. 1 is an exploded schematic perspective view illustrating an immunochromatographic kit 100 according to an embodiment of the present invention.

As illustrated in FIG. 1, the immunochromatographic kit 100 of the present embodiment is formed by including an inspection strip 1 including an insoluble carrier 2 for spreading specimen liquid, a first pot 40 enclosing a first amplification liquid for signal amplification, and a second pot 50 enclosing a second amplification liquid in a housing case 9. The housing case 9 includes a lower case 10 including an insoluble carrier accommodation portion 11 in which the insoluble carrier 2 is mounted, an upper case 20 being fitted with the lower case 10, and a flow path-forming member 65 being disposed between the upper case 20 and the lower case 10. Meanwhile, in the present embodiment, the upper case 20 has a pore for dropwise addition of specimen liquid 21 at a predetermined location above the inspection strip 1.

Figure 2:
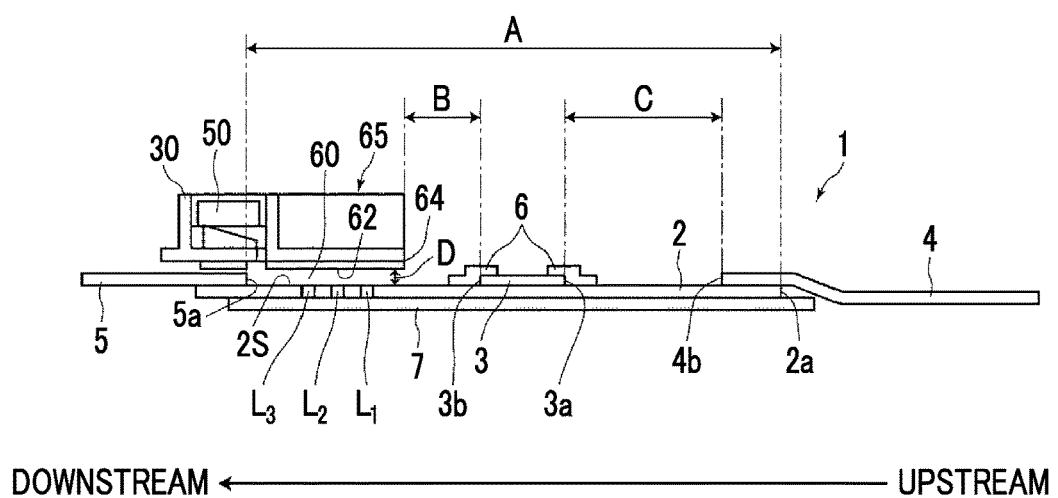
FIG. 2 is a schematic sectional view illustrating a positional relationship between an inspection strip and a middle member integrally formed with a flow path-forming member.

FIG. 2 is a schematic sectional view illustrating the disposition of the inspection strip 1 and the flow path-forming member 65.

The flow path-forming member 65 has one surface 62 forming a gap 60 that guides the second amplification liquid which is added dropwise onto the insoluble carrier 2 onto an inspection region described below between a surface 2S of the insoluble carrier 2 and the flow path-forming member, and, in the present embodiment, is integrally formed with a middle member 30 which accommodates the second pot 50 and has a pot accommodation portion 32 including on the bottom surface an amplification liquid-filling hole 34 for adding a second amplification liquid 51 dropwise onto the insoluble carrier 2. Meanwhile, the middle member 30 having the pot accommodation portion 32 and the flow path-forming member 65 may be constituted as separate bodies, but are preferably integrally constituted since it is possible to suppress an increase in the number of components. Hereinafter, in the present embodiment, the middle member 30 includes the flow path-forming member 65, that is, the flow path-forming member 65 constitutes a part of the middle member 30. That is, in the present embodiment, the housing case 9 is constituted of the lower case 10 having the strip accommodation portion 11 in which the inspection strip 1 is mounted, the upper case 20 having the pore for dropwise addition of specimen liquid 21 at the predetermined location above the inspection strip 1, and the middle member 30 being disposed between the lower case 10 and the upper case 20.

In FIG. 1, for easier understanding of the inside, the housing case 9 is illustrated as being exploded into components of the upper case 20, the middle member 30, and the lower case 10, but these components are fitted together and used as a single body in actual use.

As illustrated in FIG. 2, the inspection strip 1 includes the insoluble carrier 2 spreading specimen liquid, a label-holding pad 3 including a label substance modified with a first substance bondable to a test substance fixed on the insoluble carrier 2, a liquid-sending pad 4 being disposed in contact with one end 2a of the insoluble carrier 2 and sending a first amplification liquid 41 to the insoluble carrier 2, and an absorption pad 5 disposed in contact with the other end of the insoluble carrier 2. The insoluble carrier 2 is fixed to and supported by a back pressure-sensitive adhesion sheet 7. In addition, the insoluble carrier 2 sequentially has an inspection region $L_1$ including a second substance being bonded to a test substance, a confirmation region $L_2$ including a substance bondable to the first substance, and an amplification index region $L_3$ including a substance being reacted with the first amplification liquid from the label-holding pad 3 side between the label-holding pad 3 and the absorption pad 5.

Meanwhile, in the present specification, there are cases in which the insoluble carrier 2 obtained by forming the inspection region $L_1$, the confirmation region $L_2$, and the amplification index region $L_3$ is referred to as a chromatographic carrier. In addition, in the present specification, as illustrated in FIGS. 1 and 2, the liquid-sending pad 4 side is defined as upstream and the absorption pad 5 side is defined as downstream. Upper portions and lower portions are defined on the basis of the vertical direction on the paper of FIG. 1.

In the present embodiment, a distance A between the upstream-side end (hereinafter, the upstream end 2a), which is the above-described end 2a, of the insoluble carrier 2 and the upstream-side end (upstream end) 5a of the absorption pad 5 is 44 mm or more and 64 mm or less (from 44 mm to 64 mm). When this distance A is 44 mm or more, the sensitivity after amplification is favorable, and, when the distance is 64 mm or less, it becomes possible to set the inspection time to 15 minutes or shorter, which is preferable. A more preferred range is 49 mm or more and 59 mm or less (from 49 mm to 59 mm).

In the present embodiment, the water absorption force of the absorption pad 5 is 45 µL/minute or more and 90 µL/minute or less (from 45 µL/minute to 90 µL/minute). As the absorption pad 5, it is necessary to use a pad which absorbs specimen liquid supplied to the insoluble carrier 2, the first amplification liquid 41, and the second amplification liquid 51 and has a fast absorption rate (strong water absorption force) in order to complete inspection within a short period of time. When the water absorption force is 45 µL/minute or more, it becomes possible to set the inspection time to 15 minutes or shorter, and, when the water absorption force is 90 µL/minute or less, it is possible to constitute compact kits without excessively increasing the thickness of the absorption pad, which is preferable. A more preferred range is 65 µL/minute or more and 75 µL/minute or less (from 65 µL/minute to 75 µL/minute). Meanwhile, the definition and the measurement method of the water absorption force will be described below.

A distance B between the upstream-side end (upstream end) 64 of the surface 62 of the flow path-forming member 65 which forms the gap 60 between the surface 2S of the insoluble carrier 2 and the surface and the downstream-side end (downstream end) 3b of the label-holding pad 3 is 1 mm or more and 19 mm or less (from 1 mm to 19 mm). When this distance B is 1 mm or more, it is possible to suppress specimen liquid which is added dropwise onto the label-holding pad 3 entering the gap 60 and avoid the occurrence of abnormal amplification, which is preferable. When the distance is 19 mm or less, it becomes possible to set the inspection time to 15 minutes or shorter, which is preferable. Meanwhile, here, the upstream end 64 of the surface 62 corresponds to the upstream end of the gap 60 which is formed by the surface 2S of the insoluble carrier 2 and the surface 62 of the flow path-forming member 65.

Regarding a distance D of the gap 60 between the surface 62 of the flow path-forming member 65 and the surface 2S of the insoluble carrier 2, in order to enable uniform and rapid second amplification without any concentration unevenness, it is necessary to uniformly wet the inside of the gap 60 with the second amplification liquid and rapidly fill the inside of the gap 60 with the second amplification liquid. In order to realize what has been described above, the distance D of the gap 60 is preferably 0.01 mm or more and 1.00 mm or less.

A distance C between the upstream-side end (upstream end) 3a of the label-holding pad 3 and the downstream-side end (downstream end) 4b of the liquid-sending pad 4 is preferably 12 mm or more and 30 mm or less (from 12 mm to 30 mm). When this distance C is 12 mm or more, uneven amplification is not caused by the mixing of specimen liquid and the first amplification liquid 41, and, when the distance is 30 mm or less, it is possible to shorten the inspection time, which is preferable.

As the insoluble carrier 2, it is possible to use, for example, a nitrocellulose membrane or the like. In addition, the back pressure-sensitive adhesion sheet 7 to which the insoluble carrier 2 is fixed is a sheet-like base material a surface of which the insoluble carrier 2 is attached to is a pressure-sensitive adhesive surface.

The migration rate of specimen liquid in the insoluble carrier is defined by the time necessary for the specimen liquid to migrate one centimeter which is obtained by measuring the time necessary for water to flow through a 4 cm-long insoluble carrier 2 in terms of the capillary flow rate. In the present embodiment, it is preferable to use an insoluble carrier having a capillary flow rate of 120 to 180 seconds/cm. When the capillary flow rate is 120 seconds/ minute or more, it becomes possible to cause the second substance and a test substance on the inspection region to be sufficiently reacted with each other and cause substances bondable to the first substance modifying the label substance and the first substance to be sufficiently reacted with each other, which is preferable. On the other hand, when the capillary flow rate is 180 seconds/cm or less, it is possible to rapidly migrate specimen liquid in the insoluble carrier, and a rapid treatment completing inspection within an inspection time of 15 minutes or shorter becomes possible, which is preferable.

The insoluble carrier 2 preferably has a length of approximately 50 mm or more and 70 mm or less in the longitudinal direction.

The label-holding pad 3 is fixed to the longitudinal-direction central portion of the insoluble carrier 2. As the label substance, it is possible to use, for example, a gold colloid having a diameter of 50 nm (EM. GC50 manufactured by Boston Biomedical Inc.). When the surface of the label substance is modified with a substance being bonded to a test substance, it is possible to form bodies bonded to the test substance.

The label substance is not limited to what has been described above, metal sulfides that can be used in ordinary chromatography, colored particles that are used in immune agglutination, and the like can be used, and, particularly, metal colloids are preferred. Examples of the metal colloids include gold colloids, silver colloids, platinum colloids, iron colloids, aluminum hydroxide colloids, complex colloids thereof, and the like. Particularly, at appropriate particle diameters, gold colloids and silver colloids are preferred since they are red and yellow respectively, and, among them, gold colloids are most preferred.

As illustrated in FIG. 2, two sides of the label-holding pad 3 on the upstream side and the downstream side are preferably fixed to the insoluble carrier 2 using a film-like fixation member 6 made of an enclosing film or the like. Portions not covered with the film-like fixation member 6 correspond to regions to which test substance solutions (specimen liquid) are attached in a scattered manner. Meanwhile, the two sides that are fixed to the label-holding pad 3 are not limited to the upstream side and the downstream side illustrated in FIG. 2 and may be two sides of the insoluble carrier which are parallel to the longitudinal direction. In addition, the number of sides of the label-holding pad 3 which are covered with the film-like fixation member 6 and are fixed to the insoluble carrier is not limited two and may be three or four.

When the label-holding pad 3 is fixed to the insoluble carrier in at least two sides, handleability in stages for producing the inspection strip 1 improves and there are no cases in which measurement accuracy is deteriorated due to misalignment caused in a case in which the label-holding pad is stricken by unconsidered impacts while being transported, used, or the like. In addition, when at least two sides are covered with the film-like fixation member 6 and are fixed to the insoluble carrier 2, there are no cases in which the specimen liquid (test substance solution) being added dropwise to the label-holding pad 3 spills over the label-holding pad 3, and it is possible to transfer all of the specimen liquid to the insoluble carrier 2 through the label-holding pad 3, and thus it becomes possible to effectively subject specimen liquid to measurement.

Figure 3A:
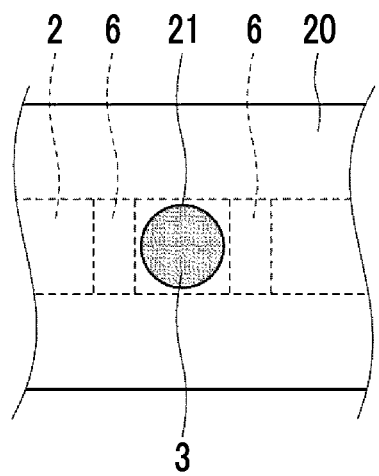
FIG. 3A is a schematic plan view illustrating part of a pore for dropwise addition of specimen liquid in a housing case of the immunochromatographic kit.
Figure 3B:
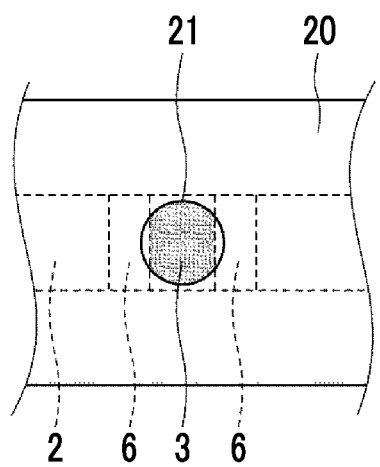
FIG. 3B is a schematic plan view illustrating part of the pore for dropwise addition of specimen liquid in the housing case of the immunochromatographic kit.

Meanwhile, it is preferable to determine the locations of the upper case 20 and the inspection strip 1 so that all of the region of the inspection strip 1 facing the pore for dropwise addition of specimen liquid 21 of the upper case 20 becomes the label-holding pad 3. In addition, regarding the film-like fixation member 6 fixing the label-holding pad 3 to the insoluble carrier 2, it is particularly desirable to determine the attachment location of the film-like fixation member 6 so that the region of the label-holding pad 3 visible from the pore for dropwise addition of specimen liquid 21 in the upper case 20 is not covered with the film-like fixation member 6 as illustrated in FIG. 3A. Compared with a case in which the label-holding pad 3 visible from the pore for dropwise addition of specimen liquid 21 in the upper case 20 is covered with the film-like fixation member 6 as illustrated in FIG. 3B, it becomes possible to add all of the specimen liquid added dropwise from the pore 21 dropwise onto the label-holding pad 3 and label all of the test substance in the specimen liquid without wasting the test substance.

Meanwhile, since the film-like fixation member is an insoluble substance, even when the film-like fixation member 6 is disposed so as to extend toward the flow path-forming member 65, there are no cases in which the specimen liquid enters the gap 60 between the flow path-forming member 65 and the insoluble carrier 2 through the film-like fixation member.

The inspection region $L_1$ is a label substance supplement region in which the second substance being bonded to a test substance is included and the label substance bonded to the test substance is supplemented through the test substance. For example, in a case in which it is intended to detect influenza A-type viruses or biomarkers thereof as a test substance, for example, an aspect in which the inspection region $L_1$ is constituted of antibody immobilization lines in which anti-influenza A-type monoclonal antibodies (Anti-Influenza A SPTN-5 7307, manufactured by Medix Biochemica) are linearly immobilized by means of physical adsorption is preferred.

When a test substance and a complex body to which the label substance is bonded through the first substance arrive at this inspection region $L_1$, the second substance and the test substance are uniquely bonded to each other, and the label substance is supplemented through the test substance and the first substance. Meanwhile, the label substance that does not constitute the complex body with the test substance is not supplemented to the inspection region $L_1$ and simply passes through.

The confirmation region $L_2$ is a region which includes substances bondable to the first substance and is intended to confirm the completion of the spread of the specimen liquid from the supplement of the label substance through the first substance which has been spread into the insoluble carrier 2 from the label-holding pad 3 together with the specimen liquid and has passed through the inspection region $L_1$. For example, in a case in which it is intended to detect influenza A-type viruses or biomarkers thereof as a test substance, for example, an aspect in which antimouse IgG antibodies (antimouse IgG(H+L), rabbit F(ab')2, Product No. 566-70621, manufactured by Wako Pure Chemical Industries, Ltd.) are linearly immobilized by means of physical adsorption is preferred.

The amplification index region $L_3$ is a region which includes a substance being reacted with the first amplification liquid 41, is reacted with the first amplification liquid 41 and thus produces or changes color, thereby indicating the spread of the first amplification liquid 41 to the region, and serves as an index of timing for the dropwise addition of the second amplification liquid 51. For example, in a case in which a mixed aqueous solution of an aqueous solution of iron nitrate and citric acid (038-06925 manufactured by Wako Pure Chemical Industries, Ltd.) is used as the first amplification liquid 41, an aspect in which the amplification index region $L_3$ is constituted of coloring reagent immobilization lines in which bromocresol green (manufactured by Wako Pure Chemical Industries, Ltd.) is linearly immobilized is preferred. At this time, when the first amplification liquid 41 arrives at the amplification index region $L_3$, the color of the region $L_3$ changes from green to orange. This color change can be considered as an index indicating that the inspection region $L_1$ and the confirmation region $L_2$ are sufficiently wetted with the first amplification liquid 41.

The substance being reacted with the first amplification liquid 41 is a coloring reagent for detecting the first amplification liquid 41, and, for example, compounds which are reacted with ions and produce color are preferably used. The details of the first amplification liquid 41 will be described below, and, in a case in which the first amplification liquid 41 includes divalent iron ions ($Fe^{2+}$), it is possible to use compounds which are reacted with $Fe^{2+}$ ions and produce color. As the compounds which are reacted with $Fe^{2+}$ ions and produce color, it is possible to use compounds capable of producing color by forming complexes with $Fe^{2+}$ ions. As specific examples of the compounds which are reacted with $Fe^{2+}$ ions and produce color, it is possible to use compounds having a phenanthroline skeleton [for example, 1,10-phenanthroline, 5-methyl phenanthroline, 5-nitrophenanthroline, bathrophenanthroline (4,7-diphenyl-1,10-phenanthroline), bathrophenanthroline disulfate, and the like] or compounds having a bipyridine skeleton [for example, 2,2'-bipyridine and the like], and, preferably, compounds having a phenanthroline skeleton can be used. In addition, in a case in which the pH of an aqueous solution including a test substance and the pH of the first amplification liquid 41 are different from each other, it is preferable to use reagents having hue being changed by proton-induced structural changes in order to detect the first amplification liquid 41. Particularly, in a case in which the first amplification liquid 41 is acidic (the pH is lower than 7, and the concentration of protons is high), as an pH indicator for the acidic region, it is preferable to appropriately select and use compounds which are reacted with $H^+$ ions, which are a well-known coloring reagent, and thus produce color (for example, diazo-based coloring agents such as methyl orange, methyl red, congo red, and methyl yellow and sultone-based coloring agents such as thymol blue, bromocresol green, bromocresol purple, and bromothymol blue) in accordance with the pH of an aqueous solution including an amplification reagent. Among these, 1,10-phenanthroline, bathrophenanthroline, or bromocresol green is more preferably used.

Furthermore, the constitutions of the respective components constituting the immunochromatographic kit 100, a constitution in which the components are integrated together, and application formats thereof will be described.

Figure 4:
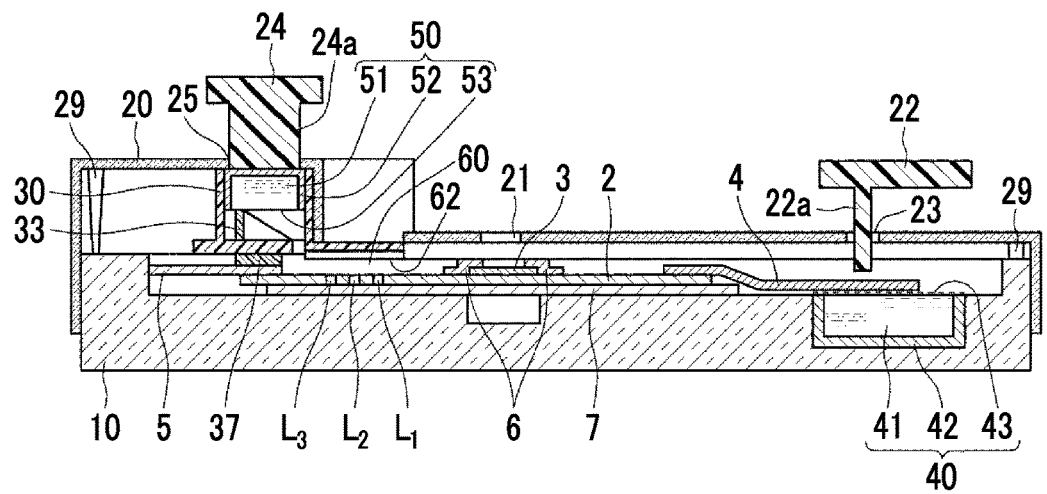
FIG. 4 is a schematic sectional view of a movable member in the immunochromatographic kit illustrated in FIG. 1 before being pressed.
Figure 5:
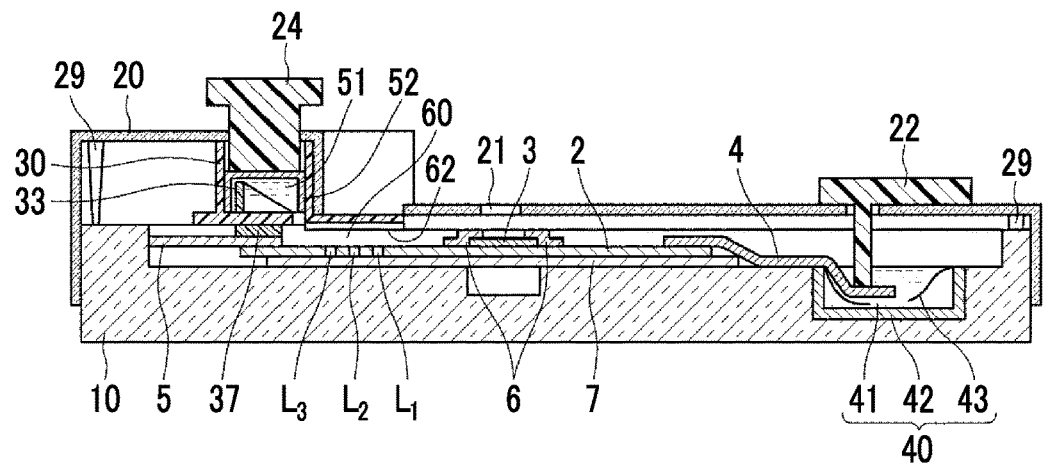
FIG. 5 is a schematic sectional view of the movable member in the immunochromatographic kit illustrated in FIG. 1 after being pressed.
Figure 6:
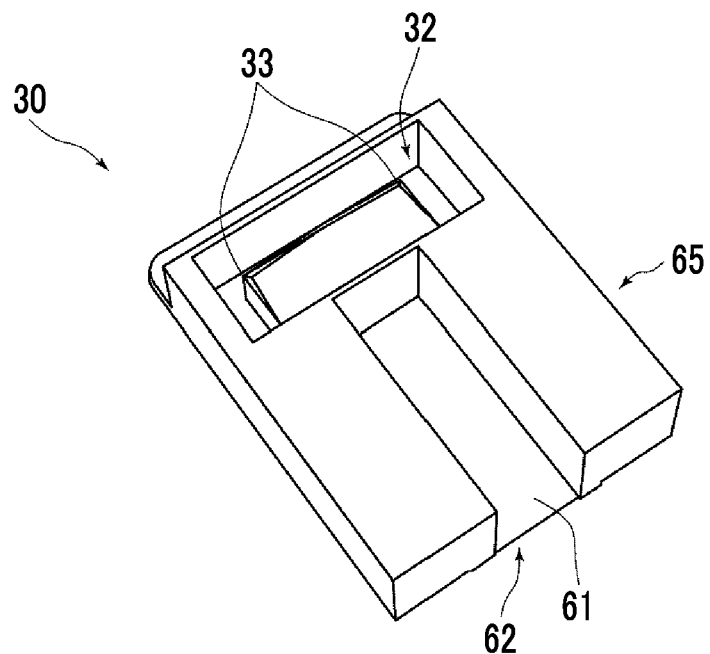
FIG. 6 is a schematic perspective view of a constitution of an upper case side of the middle member in the immunochromatographic kit illustrated in FIG. 1.
Figure 7:
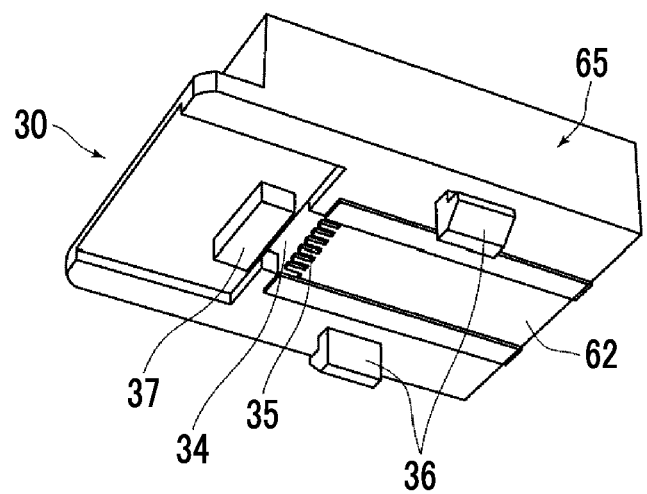
FIG. 7 is a schematic perspective view of a constitution of a lower case side of the middle member in the immunochromatographic kit illustrated in FIG. 1.
Figure 8:
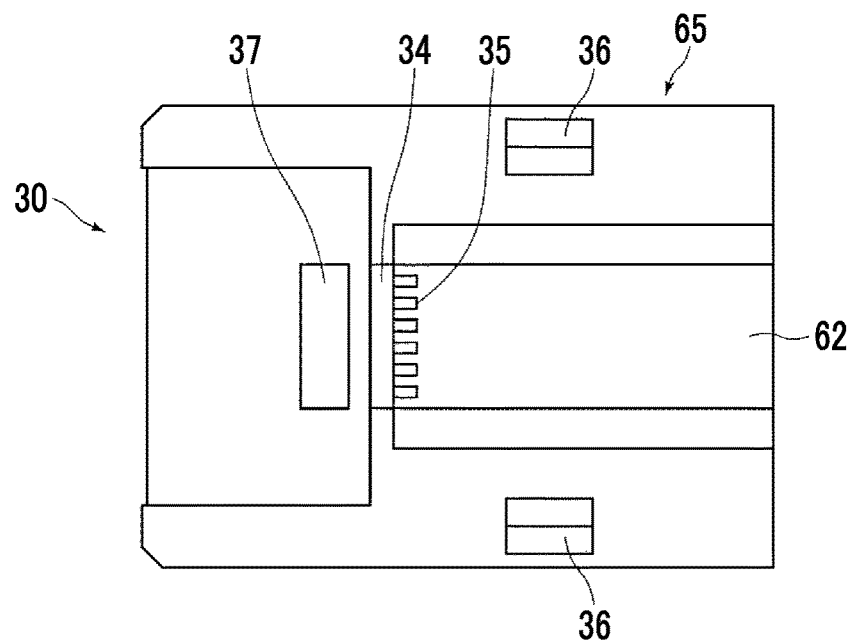
FIG. 8 is a schematic bottom surface view illustrating a lower case-side surface of the middle member in the immunochromatographic kit illustrated in FIG. 1.

FIGS. 4 and 5 are schematic sectional views illustrating the aspects of the immunochromatographic kit 100 before signal amplification and after signal amplification, FIG. 6 is a perspective view facing the upper surface (upper case side) of the middle member 30, and FIGS. 7 and 8 are a schematic perspective view and a schematic bottom surface view facing the lower surface (lower case side) of the middle member 30.

The first pot 40 enclosing the first amplification liquid 41 is obtained by filling a container 42 having an opening on one surface constituted of, for example, a resin material with the amplification liquid 41 and covering the opening of the container 42 with a breakable sheet member 43.

Similarly, the second pot 50 enclosing the second amplification liquid 51 is also obtained by filling a container 52 having an opening on one surface constituted of, for example, a resin material with the second amplification liquid 51 and covering the opening of the container 52 with a breakable sheet member 53.

As the sheet members 43 and 53 in the first pot 40 and the second pot 50, aluminum foils, aluminum sheets, and the like are preferably used.

As a method for amplifying the signals of metal-based label substances such as metal colloids, it is preferable to use a method in which silver ions and a reducing agent for the silver ions are brought into contact with a label substance, the silver ions are reduced by the reducing agent so as to generate silver particles, and the silver particles deposit on the label substance using the label substance as a nucleus, thereby amplifying signals using the label substance (hereinafter, silver amplification).

In order to realize the silver amplification, a reducing agent liquid including a reducing agent for silver ions may be used as the first amplification liquid 41, and a solution including silver ions may be used as the second amplification liquid 51.

As the reducing agent for silver ions which is a preferred aspect of the first amplification liquid 41, it is possible to use any of an inorganic material, an organic material, or a mixture as long as the material is capable of reducing silver ions to silver.

Examples of inorganic reducing agents include reducing metal salts and reducing metal complexes which are capable of changing the atomic value with metal ions such as $Fe^{2+}$, $V^{2+}$, or $Ti^{3+}$. In a case in which an inorganic reducing agent is used, it is necessary to exclude influences on reducing properties by forming a complex of oxidized ions or removing the oxidized ions by means of reduction. For example, in a case in which $Fe^{2+}$ is used as the reducing agent, it is possible to form a complex of $Fe^{3+}$ which is a suboxide using citric acid or ethylenediaminetetraacetic acid (EDTA) and exclude influences on reducing properties. In the present system, the above-described inorganic reducing agent is preferably used, and a metal salt of $Fe^{2+}$ is particularly preferred.

Regarding additional examples of the reducing agent, it is possible to refer to the description of JP2014-66674A.

A preferred solution including silver ions as the second amplification liquid 51 is a solution in which a silver ion-containing compound is dissolved in a solvent. As the silver ion-containing compound, it is possible to use organic silver salts, inorganic silver salts, or silver complexes. Inorganic silver salts or silver complexes are preferred. As the inorganic silver salts, it is possible to use silver ion-containing compounds having a high solubility in solvents such as water, and examples thereof include silver nitrate, silver acetate, silver lactate, silver butyrate, silver thiosulfate, and the like. Silver nitrate is particularly preferred. The silver complexes are preferably silver complexes coordinated with ligands having a water-soluble group such as a hydroxyl group or a sulfone group, and examples thereof include silver hydroxythioether and the like.

As illustrated in FIGS. 1 and 4, the lower case 10 and the middle member 30 are engaged with each other by inserting an engagement protrusion portion 36 formed in the middle member 30 into an engagement opening 16 which is formed in the lower case 10 and corresponds to the engagement protrusion portion 36. In addition, the lower case 10 and the upper case 20 are fitted with each other by inserting fitting protrusion portions 29 formed at four corners of the upper case 20 into fitting openings 19 which are formed in the lower case 10 and respectively correspond to the fitting protrusion portions 29 in a state in which the lower case 10 and the middle member 30 are engaged with each other.

In the lower case 10, as an accommodation portion in which the inspection strip 1 is disposed, an insoluble carrier accommodation portion 11 in which the insoluble carrier 2 is mounted is provided, and an absorption pad accommodation portion 13 in which the absorption pad 5 is mounted is provided on the downstream side of the insoluble carrier accommodation portion. In addition, a first pot accommodation portion 12 in which the first pot 40 is accommodated is provided on the upstream side of the insoluble carrier accommodation portion 11.

The inspection strip 1 is mounted in the accommodation portion in the lower case 10, the first pot 40 is disposed in the first pot accommodation portion 12 so that the surface having the sheet member 43 becomes the upper surface, and the liquid-sending pad 4 in the inspection strip 1 is disposed on the surface of the sheet member 43.

As illustrated in FIGS. 1 to 8, the middle member 30 has the pot accommodation portion 32 which accommodates the second pot 50 and includes on the bottom surface the amplification liquid-filling hole 34 for adding the second amplification liquid 51 dropwise onto the insoluble carrier 2. In addition, a protrusion portion 33 breaking the sheet member 53 is provided at a location facing the sheet member 53 of the second pot 50 in the pot accommodation portion 32. In the present example, the second pot 50 is disposed above the pot accommodation portion 32 so that the surface having the sheet member 53 becomes the lower surface, and the protrusion portion 33 is provided on the bottom surface of the pot accommodation portion 32 facing the sheet member 53. Between the second pot 50 and the bottom surface of the pot accommodation portion 32 in the middle member 30, for example, a spring member may be inserted so that the second pot 50 is urged toward the upper case 20 side in order to prevent the sheet member 53 in the second pot 50 from being broken by the protrusion portion 33 when the middle member 30 is mounted in the lower case 10.

In addition, ribs 35 for the amplification liquid-filling hole are provided in a portion of the middle member 30 which is adjacent to the amplification liquid-filling hole 34, and an absorption pad-pressing protrusion 37 that presses the absorption pad 5 during the engagement with the lower case 10 is provided on the rear surface side of the pot accommodation portion 32. In addition, the surface 62 of the flow path-forming member 65 is formed as a part of the middle member 30 continuously from the ribs 35. Meanwhile, the middle member 30 is disposed so that the surface 62 is located above the inspection region $L_1$, the confirmation region $L_2$, and the amplification index region $L_3$, and the surface 62 is formed of a transparent material so as to make the inspection region $L_1$, the confirmation region $L_2$, and the amplification index region $L_3$ visible from above and functions as one surface of an observation window 61.

As described above, the pore for dropwise addition of specimen liquid 21 is provided in the central portion of the upper surface of the upper case 20, and the specimen liquid is added dropwise onto the label-holding pad 3 of the inspection strip 1 from this pore 21. When the location of the label-holding pad 3 is adjusted so that the locations of the pore 21 and the label-holding pad 3 correspond to each other, it becomes possible to attach the specimen liquid onto the label-holding pad 3 in a scattered manner.

An opening 28 is provided in a location of the upper case 20 corresponding to the observation window 61 in the middle member 30 so as to prevent visibility from the observation window 61 from being impaired.

In addition, an insertion opening 23 formed of a narrow rectangular opening is provided on the upper case 20 in a location of the lower case 10 corresponding to the pot accommodation portion 12, and a first movable member 22 having a columnar portion 22a that can be inserted into the insertion opening 23 is held in a state in which the tip of the columnar portion 22a is inserted into the insertion opening 23. The first movable member 22 can be pressed into the lower portion by applying forces, and, when the movable member 22 is pressed in, the liquid-sending pad 4 is pressed and displaced, the sheet member of the first pot 40 enclosing the first amplification liquid is broken, the liquid-sending pad is pressed into the first pot, whereby it is possible to immerse the liquid-sending pad in the first amplification liquid. In this state, it becomes possible to spread the first amplification liquid onto the insoluble carrier through the liquid-sending pad.

As a mechanism for maintaining the state of the sheet member of the pot being held without being penetrated in a state in which the tip of the columnar portion 22a of the movable member 22 is inserted into the insertion opening 23 until the sheet member is pressed down by applying external forces, for example, a constitution in which a withdrawal prevention mechanism that is not easily removed from the upper case 20 is provided at the tip of the columnar portion 22a and, for example, a spring member is provided between the upper surface of the upper case 20 and a head portion 22h of the movable member 22 may be provided.

Meanwhile, the timing of applying forces to the first movable member 22 is preferably within 30 seconds from the dropwise addition of the specimen liquid onto the label-holding pad 3 on the insoluble carrier 2 and more preferably immediately after the dropwise addition. When the first amplification liquid 41 is provided to the insoluble carrier 2 at the above-described timing, the specimen liquid can be spread in a direction of the inspection region $L_1$, the confirmation region $L_2$, and the amplification index region $L_3$ using suctioning forces attributed to the capillary action of the absorption pad 5, and, at the same time, it becomes possible to spread the first amplification liquid 41 in the direction of the inspection region $L_1$, the confirmation region $L_2$, and the amplification index region $L_3$.

As described above, when a structure in which the first pot 40 is disposed below the liquid-sending pad 4 is provided, it becomes possible to store the first amplification liquid 41 in the immunochromatographic kit, supply a sufficient amount of the amplification liquid 41, and stabilize amplification conditions.

In a location of the upper case 20 which corresponds to the pot accommodation portion 32 in the middle member 30, an insertion opening 25 formed of a cross-shaped opening is provided, and the tip of a columnar portion 24a of a second movable member 24 having the columnar portion 24a having almost the same sectional shape as the insertion opening 25 is held in a state of being inserted into the insertion opening 25. The second movable member 24 is constituted to be pressed into the lower portion by applying forces, and, when the movable member 24 is pressed, the second pot 50 is moved toward the protrusion portion 33 up to a location in which the sheet member 53 of the second pot 50 is broken by the protrusion portion 33 in the pot accommodation portion 32 in the middle member 30. Therefore, the protrusion portion 33 penetrates the sheet member 53 of the second pot 50, and it becomes possible to supply the second amplification liquid 51 to the outside. The amplification liquid is added dropwise to the upper portion of the insoluble carrier 2 from the amplification liquid-filling hole 34 that is provided on the bottom surface of the pot accommodation portion 32 in the middle member 30, and it becomes possible to supply the second amplification liquid 51 to the inspection region $L_1$, the confirmation region $L_2$, and the amplification index region $L_3$ on the insoluble carrier. Meanwhile, at this time, the second amplification liquid 51 added dropwise to the upper portion of the insoluble carrier 2 from the amplification liquid-filling hole 34 fills the gap between the middle member 30 and the insoluble carrier 2, is supplied to the above of the inspection region $L_1$, the confirmation region $L_2$, and the amplification index region $L_3$ through the gap, and gradually permeates into the insoluble carrier 2.

As a mechanism for maintaining the state of the second pot 50 being held so as not to be pressed down in a state in which the tip of the columnar portion 24a of the second movable member 24 is inserted into the insertion opening 25 until the second pot is pressed down by applying external forces, similar to the case of the first movable member 22, for example, a constitution in which a withdrawal prevention mechanism that is not easily removed from the upper case 20 is provided at the tip of the columnar portion 24a and, for example, a spring member is provided between the upper surface of the upper case 20 and a head portion of the movable member 24 may be provided.

Meanwhile, in the present embodiment, the second movable member 24 moves the second pot 50 toward the protrusion portion 33 being provided in the middle member 30, but the second movable member is simply required to be capable of relatively moving the second pot with respect to the protrusion portion and may be constituted so as to move the protrusion portion without moving the second pot, thereby breaking the sheet member of the second pot with the protrusion portion or move both the second pot and the protrusion portion, thereby breaking the sheet member with the protrusion portion. For example, a constitution in which the protrusion portion disposed in the accommodation portion in the middle member is in contact with the second movable member and the protrusion portion is moved toward the sheet member by pressing the second movable member from the outside.

The sheet member of the second pot is not necessarily disposed against the inspection strip, and the constitution of the second pot and the accommodation portion accommodating the second pot is also not limited to the constitution of the present invention as long as it is possible to add the second amplification liquid flowing out from the pot due to the breakage of the sheet member dropwise onto the insoluble carrier 2 from the amplification liquid-filling hole 34 in the bottom surface of the pot accommodation portion 32.

As illustrated in FIG. 4, in a state in which the respective members of the housing case 9 are integrated together, the insoluble carrier 2 is located so that the label-holding pad 3 is located in substantially the central portion of the lower case 10, the liquid-sending pad 4 and the absorption pad 5 are disposed at one end on the upstream side and on the downstream side so as to partially overlay the insoluble carrier 2 respectively, and the disposition of the inspection strip 1 is adjusted so that the pore for dropwise addition of specimen liquid 21 in the upper case 20 is located so as to face the label-holding pad 3. The liquid-sending pad 4 overlays the insoluble carrier 2 in one end, extends without overlaying the insoluble carrier 2 on the other end, and is disposed so that this extended portion is located on the upper surface of the first pot 40 provided in the pot accommodation portion 12.

The middle member 30 is disposed on the region of the absorption pad 5 overlaying the insoluble carrier and the upper portions of the inspection region $L_1$, the confirmation region $L_2$, and the amplification index region $L_3$. The absorption pad-pressing protrusion 37 of the middle member 30 is located so as to press the absorption pad 5 in a region in which the absorption pad-pressing protrusion overlays the insoluble carrier 2, as described above, the regions $L_1$ to $L_3$ are located below the observation window 61 in the middle member 30, and the surface 62 constitutes the gap 60 between the insoluble carrier 2 and the surface. The opening 28 in the upper case 20 is located above the observation window 61. In addition, the first movable member 22 and the insertion opening 23 into which the first movable member 22 is inserted are located above the liquid-sending pad 4, and the second movable member 24 and the cross-shaped insertion opening 25 into which the second movable member 24 is inserted are located above the second pot 50.

The shape of the pot accommodation portion 32 in the middle member 30 is preferably a structure being fitted with the second pot 50 enclosing the second amplification liquid 51. When the above-described structure is provided, it becomes possible to enhance the repetitive reproducibility of the supply amount and the supply rate of the second amplification liquid 51 being supplied to the insoluble carrier 2. In addition, when a structure in which the second amplification liquid 51 is supplied onto the insoluble carrier 2 from the amplification liquid-filling hole 34 is provided, it is possible to prevent the second amplification liquid 51 from spilling out.

In addition, the second amplification liquid 51 is supplied from the above on the downstream side of the insoluble carrier 2, that is, the spreading direction of the specimen liquid, the spreading direction of the first amplification liquid 41, and the spreading direction of the second amplification liquid 51 are on the same straight line, and thus it becomes possible to absorb the three solutions of the specimen liquid including the test substance, the first amplification liquid 41, and the second amplification liquid 51 with one absorption pad 5, and designs of compact kits become possible.

<Immunochromatographic Inspection Method>

An immunochromatographic inspection method using the immunochromatographic kit 100 will be simply described.

The specimen liquid is added dropwise onto the label-holding pad 3 from the pore for dropwise addition of specimen liquid 21. In a case in which the test substance is included in the specimen liquid, the test substance and the first substance are bonded to each other in the label-holding pad 3, whereby a complex body of the test substance and the label substance is formed through the first substance, and the complex body is spread toward the absorption pad 5 side together with the specimen liquid due to the suctioning force of the absorption pad 5 and the capillary action. At the same time as or after the dropwise addition of the specimen liquid, the first movable member 22 is pressed down, the liquid-sending pad 4 is displaced, the sheet member 43 of the first pot 40 is broken, the liquid-sending pad 4 is wetted by the first amplification liquid 41, and the first amplification liquid 41 is sent. Meanwhile, the timing of the first movable member 22 being pressed down is preferably set to 30 seconds or shorter from the dropwise addition of the specimen liquid and particularly preferably immediately after the dropwise addition of the specimen liquid.

The complex body arriving at the inspection region $L_1$ is bonded to the second substance in the inspection region $L_1$ and is trapped. In addition, the first substance that is not bonded to the test substance passes through the inspection region $L_1$, arrives at the confirmation region $L_2$, is bonded to a substance being bonded to the first substance in the confirmation region $L_2$, and is trapped.

The first amplification liquid 41 arrives at the amplification index region $L_3$ through the inspection region $L_1$ and the confirmation region $L_2$. At this time, the amplification index region $L_3$ discolors, whereby it is possible to visually recognize the arrival of the first amplification liquid 41 at the amplification index region $L_3$. After the discoloration of the amplification index region $L_3$ is confirmed, the second movable member 24 is pressed down and the second amplification liquid 51 is supplied onto the insoluble carrier 2. In the present embodiment, the second amplification liquid 51 added dropwise on the downstream side of the regions $L_1$ to $L_3$ on the insoluble carrier 2 from the amplification liquid-filling hole 34 permeates into the gap 60 between the surface 62 of the flow path-forming member 65 and the surface 2S of the insoluble carrier 2 and is guided to the inspection region $L_1$ using this gap 60.

After the supply of the second amplification liquid 51 to the insoluble carrier 2, the end of a reaction is waited, and the discoloration of the inspection region $L_1$ and the confirmation region $L_2$ is confirmed through the observation window 61. The presence or absence of the test substance and the concentration thereof can be confirmed from the discoloration of the inspection region $L_1$, and whether or not inspection for measuring the test substance is succeeded can be confirmed from the discoloration of the confirmation region $L_2$. Discoloration in the inspection region $L_1$ and the confirmation region $L_2$ is caused by amplifying the signals of the label, and highly sensitive inspection can be carried out.

As described above, the use of the immunochromatographic kit 100 enables accurate inspection with this kit alone without using exclusive analyzers.

Hereinafter, preferred specific aspects of the mechanism in which the tip of the columnar portion 22a of the movable member 22 is not easily removed in a state of being inserted into the insertion opening 23 and the sheet member of the pot is held without being penetrated until the sheet member is pressed down by applying external forces will be described with reference to FIGS. 9 and 10.

First, a first aspect will be described with reference to FIG. 9. FIG. 9 is a schematic sectional view illustrating the periphery of the movable member 22 in the immunochromatographic kit 100, A illustrates the first movable member 22 before being pressed down, and B illustrates the first movable member 22 after being pressed down.

A withdrawal prevention protrusion 22b that is not easily removed from the upper case 20 is provided at the tip of the columnar portion 22a in the movable member 22. In addition, a movement prevention protrusion 22c restricting the upward movement of the movable member 22 when the movable member is inserted into the housing case toward the head portion side of the columnar portion 22a up to a predetermined depth is provided.

These protrusions 22b and 22c being provided on the columnar portion 22a are protrusion portions tempering toward the tip side, when the protrusions are inserted into the insertion opening 23 from the tapered side, the protrusions slightly contract due to elasticity and can be easily inserted; however, once being inserted into the housing case, the still-wide side of the protrusion portions is caught by the upper case 20 and cannot be withdrawn from the insertion opening 23.

Figure 9:
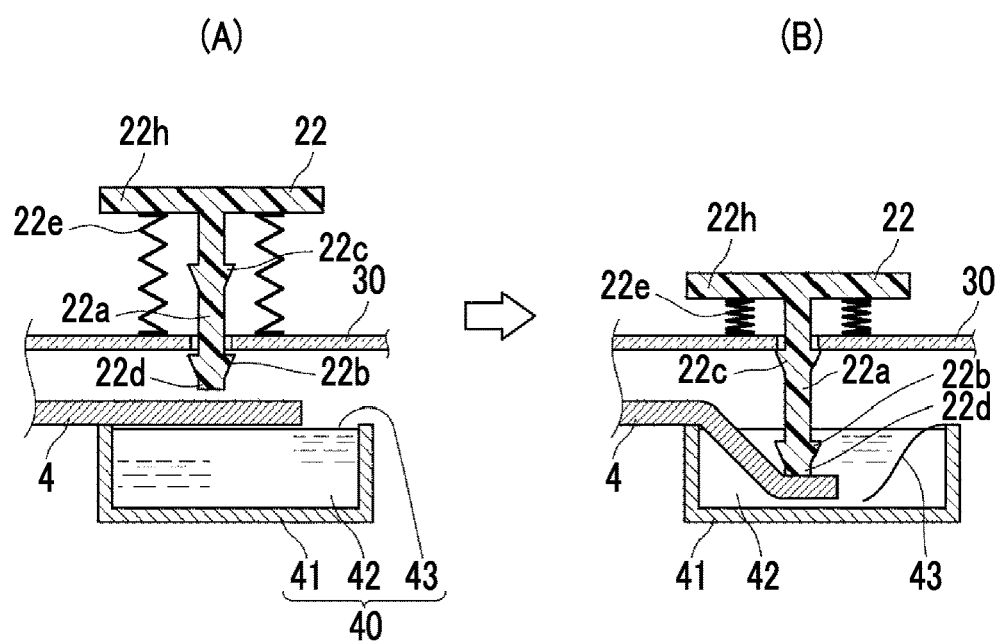
FIG. 9 is a schematic sectional view illustrating an aspect of a first movable member in the immunochromatographic kit.

A mechanism for preventing only the tip 22d of the columnar portion 22a from being inserted into the insertion opening 23 and lowered downward before the press-down of the movable member 22 can be realized using the elastic force of a spring member 22e as illustrated by A and B in FIG. 9.

Figure 10:
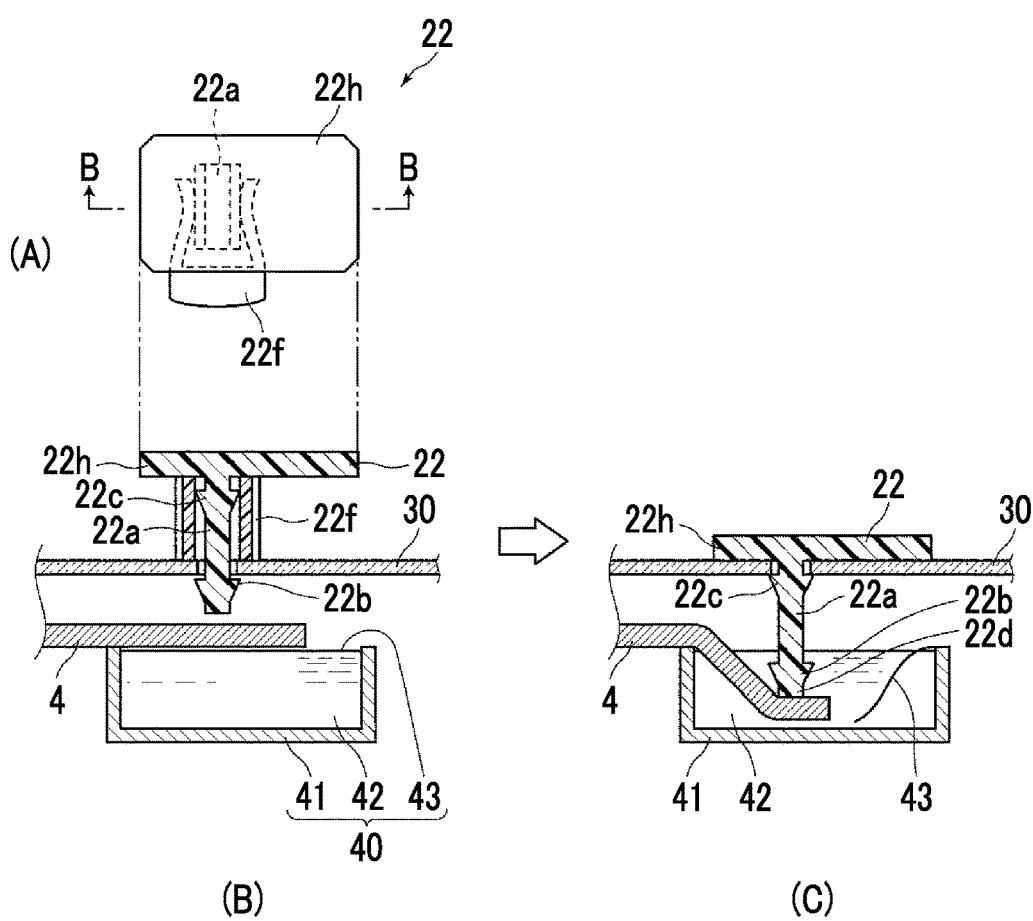
FIG. 10 is a schematic sectional view illustrating another aspect of the first movable member in the immunochromatographic kit.

FIG. 10 is a partial design modification example of the aspect illustrated in FIG. 9. In FIG. 10, A is a schematic plan view illustrating a state of the movable member 22 before being pressed down, B is a schematically sectional view along a B-B line in the schematic plan view A, and C is a schematic sectional view illustrating a state of the movable member 22 after being pressed down The withdrawal prevention protrusion 22b and the movement prevention protrusion 22c being provided in the columnar portion 22a in the movable member 22 are the same as those in FIG. 9.

In the present design modification example, the mechanism for preventing only the tip 22d of the columnar portion 22a from being inserted into the insertion opening 23 and lowered downward before the press-down of the movable member 22 is different. Here, a removable clip member 22f for press-down prevention is provided. Before the movable member is pressed down, the clip member 22f, the clip member 22f is inserted between the head portion 22h of the movable member 22 and the upper surface of the upper case 20 so as to sandwich the columnar portion 22a, and, when the movable member 22 is pressed down, the movable member 22 is pressed down in a state of including the clip member 22f The constitution is easier than that including the spring member, and, since the movable member 22 does not move even when forces are applied to the movable member 22 in a state of including the clip member 22f, the sheet member of the first pot is not broken by the movable member 22 even when being stricken by somewhat impacts during transportation and the like, which is preferable.

Meanwhile, as the mechanism in which the tip of the columnar portion 24a of the second movable member 24 is not easily removed in a state of being inserted into the insertion opening 25 and the second pot is held without being moved until the second pot is pressed down by applying external forces, the above-described constitution can be used in the same manner.

Meanwhile, the immunochromatographic kit of the present invention may include a set or a part thereof which is necessary for inspection such as a pot including a test body extraction liquid including an assistant chemical assisting the extraction of test bodies or a pot including a test body dilution liquid, a drying agent or a deoxidizer helping the storage of the kit, attached documents such as manuals, and test body-collecting tools such as ear sticks.

EXAMPLES

Hereinafter, examples and comparative examples of the immunochromatographic kit of the present invention will be described. Immunochromatographic kits of the examples and the comparative examples are immunochromatographic kits for influenza virus antigen detection for detecting influenza virus antigens as a test substance.

(1) Production of Immunochromatographic Kit (1-1) Production of Anti-Influenza A-Type Antibody-Modified Gold Colloid as Label Substance Modified with First Substance Bondable to Test Substance 1 mL of a solution of 160 µg/mL of an anti-influenza A-type monoclonal antibody (Anti-Influenza A SPTN-5 7307, manufactured by Medix Biochemica) was added to and stirred with a gold colloid solution having a pH adjusted by adding 1 mL of 50 mmol/L of $KH_2PO_4$ buffer (pH 7.5) to 9 mL of a gold colloid solution (Product No.: EM. GC50, manufactured by Boston Biomedical Inc.) having a diameter of 50 nm. After the solution mixture was left to stand for ten minutes, 550 µL of an aqueous solution of 1% polyethylene glycol (PEG; weight-average molecular weight (Mw.): 20,000, Product No. 168-11285, manufactured by Wako Pure Chemical Industries, Ltd.) was added to and stirred with the solution mixture, and subsequently, 1.1 mL of an aqueous solution of 10% bovine serum albumin (BSA); FractionV, Product No.: A-7906, manufactured by Sigma-Aldrich Co. LLC.) was added to and stirred with the solution mixture. After this solution was centrifuged (using himacCF16RX, manufactured by Hitachi Ltd.) at a centrifugal acceleration of 8,000×g and 4° C. for 30 minutes, the supernatant was removed except for approximately 1 mL, and the gold colloid was re-dispersed using an ultrasonic washer. After that, the gold colloid was dispersed in 20 mL of a gold colloid preservative solution (20 mmol/L Tris-HCl (Tris hydrochloric acid) buffer (pH 8.2), 0.05% PEG (Mw. 20,000), 150 mmol/L NaCl, 1% BSA), was again centrifuged at 8,000×g and 4° C. for 30 minutes, then, the supernatant was removed except for approximately 1 mL, and the gold colloid was re-dispersed using an ultrasonic washer, thereby obtaining an antibody-modified gold colloid (50 nm) solution.

(1-2) Production of Anti-Influenza A-Type Antibody-Modified Gold Colloid-Holding Pad as Label-Holding Pad The influenza A-type antibody-modified gold colloid produced in (1-1) was diluted with water so that the concentration of the Tris-HCl buffer (pH: 8.2) reached 20 mmol/L, the concentration of PEG (Mw. 20,000) reached 0.05 mass %, the concentration of sucrose reached 5 mass %, and the optical density of the gold colloid at 520 nm reached 0.1 when the light wavelength was set to 10 mm, thereby producing a gold colloid coating fluid. This coating fluid was uniformly applied onto 12 mm×300 mm-cut glass fiber pads (Glass Fiber Conjugate Pad, manufactured by EMD Millipore Corporation) at 0.8 mL per pad and was dried at reduced pressure for 24 hours, thereby obtaining an influenza A-type antibody-modified gold colloid-holding pad.

(1-3) Production of Chromatographic Carrier

As the insoluble carrier 2, a 60 mm×300 mm-cut nitrocellulose membrane (with a plastic backing, HiFlow Plus HF120, manufactured by EMD Millipore Corporation) was used, and the inspection region $L_1$, the confirmation region $L_2$, and the amplification index region $L_3$ were formed on this membrane using a method as described below, thereby producing a chromatographic carrier.

An anti-influenza A-type monoclonal antibody (Anti-Influenza A SPTN-5 7307, manufactured by Medix Biochemica) solution produced so as to be 1.5 mg/mL was applied in a line shape to a location 15 mm away from one of two long sides (300 mm) of the 60 mm×300 mm rectangular nitrocellulose membrane toward the other side, thereby producing the inspection region $L_1$. Furthermore, similarly, an antimouse IgG antibody (antimouse IgG(H+L), rabbit F(ab')2, Product No. 566-70621, manufactured by Wako Pure Chemical Industries, Ltd.) solution produced so as to be 0.2 mg/mL was applied in a line shape to a location 11 mm away from one side toward the other side, thereby producing the confirmation region $L_2$. Furthermore, similarly, bromocresol green (manufactured by Wako Pure Chemical Industries, Ltd.) produced so as to be 30 mmol/mL was applied in a line shape to a location 9 mm away from one side toward the other side, thereby producing the amplification index region $L_3$. After the application of the respective components, the nitrocellulose membrane was dried at 50° C. for 30 minutes using a warm air-type dryer. 500 mL of a blocking liquid (50 mmol/L of a boric acid buffer (pH: 8.5) containing 0.5 mass % casein (derived from milk, Product No. 030-01505, manufactured by Wako Pure Chemical Industries, Ltd.)) was fed into a bat, the membrane was immersed therein and was left to stand for 30 minutes. After that, the nitrocellulose membrane was moved to and immersed in 500 mL of a washing and stabilizing liquid (50 mmol/L of Tris-HCl buffer (pH: 7.5) including 0.5 mass % sucrose and 0.05 mass % sodium cholate) fed into another bat and was left to stand for 30 minutes. After that, the nitrocellulose membrane was removed from the liquid and was dried at an environment of 25° C. for 24 hours.

In the present example, the anti-influenza A-type antibody corresponds to the second substance being bonded to the test substance, the antimouse IgG antibody corresponds to the substance bondable to the first substance, and the bromocresol green corresponds to the substance being reacted with the first amplification liquid.

(1-4) Production of Inspection Strip

The chromatographic carrier (the insoluble carrier 2 on which the inspection region $L_1$, the confirmation region $L_2$, and the amplification index region $L_3$ were formed) produced in (1-3) was attached to a back pressure-sensitive adhesion sheet (60 mm×300 mm (manufactured by Nippon Flour Mills Co., Ltd.)). Next, the gold colloid antibody-holding pad produced in (1-2) as the label-holding pad 3 was disposed at a predetermined place near the center of the insoluble carrier 2, and a 4 mm-wide enclosing film was attached to both ends of the gold colloid-holding pad so that the film and the gold colloid-holding pad overlaid each other 1.5 mm, thereby fixing the gold colloid-holding pad to the insoluble carrier 2. The liquid-sending pad 4 (a 25 mm×300 mm-cut glass fiber pad (Glass Fiber Conjugate Pad, manufactured by EMD Millipore Corporation) was attached to the insoluble carrier 2 on the upstream side so that the liquid-sending pad 4 and the insoluble carrier 2 overlaid each other 7 mm. The member produced in the above-described manner was cut using a guillotine-type cutter (CM4000, manufactured by Nippon Flour Mills Co., Ltd.)) parallel to a direction perpendicular to the long side (300 mm) so as to obtain a width of 5 mm, thereby producing 60 inspection strips (however, no absorption pad was included).

(1-5) Production of Amplification Liquid (1-5-1) Production of First Amplification Liquid (Reducing Agent Solution)

23.6 mL of an aqueous solution of 1 mol/L of iron nitrate produced by dissolving iron (III) nitrate nonahydrate (manufactured by Wako Pure Chemical Industries, Ltd., 095-00995) in water and 13.1 g of citric acid (manufactured by Wako Pure Chemical Industries, Ltd., 038-06925) were dissolved in 290 g of water. Once the components were fully dissolved, 36 mL of nitric acid (10 weight %) was added thereto while stirring the solution using a stirrer, 60.8 g of iron (II) ammonium sulphate hexahydrate (manufactured by Wako Pure Chemical Industries, Ltd., 091-00855) was added thereto, and this mixture was used as a reducing agent solution that is the first amplification liquid 41.

(1-5-2) Production of Second Amplification Liquid (Silver Ion Solution)

8 mL of a silver nitrate solution (including 10 g of silver nitrate) and 24 mL of an aqueous solution of 1 mol/L of iron nitrate were added to 66 g of water. Furthermore, this solution and a solution obtained by dissolving 5.9 mL of nitric acid (10 weight %), 0.1 g of dodecylamine (manufactured by Wako Pure Chemical Industries, Ltd., 123-00246), and 0.1 g of a surfactant $C_{12}H_{25}$—$C_6H_4$—O—$(CH_2CH_2O)_{50}H$ in 47.6 g of water in advance were mixed together, and this solution was used as a silver ion solution that is the second amplification liquid 51.

(1-6) Production of Absorption Pad

Sixty 12 mm×10 mm-cut glass fiber pads (glass filter paper, manufactured by Advantech Co., Ltd.) were prepared and was used as the absorption pad 5 for the respective inspection strips.

(1-7) Production of Components of Immunochromatographic Kit

The lower case 10, the upper case 20, and the middle member 30 constituting the housing case 9 illustrated in FIG. 1 and the first movable member 22, the second movable member 24, the first pot 40 accommodating the first amplification liquid 41, and the second pot 50 accommodating the second amplification liquid 51 which are provided in the housing case 9 were respectively produced by means of injection molding using polypropylene as materials.

Hereinafter, first, examples and comparative examples of a first invention (Examples 1 and 2 and Comparative Example 1 and 2) will be described.

(1-8-1) Production of Immunochromatographic Kit of Example 1

The lower case 10, the inspection strip produced in (1-4), and the absorption pad produced in (1-6) were fixed as illustrated in FIG. 4. Next, the first pot 40 and the second pot 50 were respectively filled with the first amplification liquid and the second amplification liquid produced in (1-5-1) and (1-5-2), were enclosed with aluminium foils as the sheet member, and were mounted in the lower case 10 and the middle member 30 respectively as illustrated in FIG. 4. The first movable member 22 and the second movable member 24 were mounted in the upper case 20 through the insertion openings 23 and 25 respectively, and the lower case 10, the middle member 30, and the upper case 20 were assembled together as illustrated in FIG. 4, thereby producing an immunochromatographic kit. Meanwhile, at this time, the enclosing film fixing the gold colloid antibody-holding pad was disposed so as to be invisible from the pore for dropwise addition of specimen liquid (refer to FIG. 3A). That is, the immunochromatographic kit of Example 1 was constituted so that a region facing the pore for dropwise addition of specimen liquid was not covered with the enclosing film of the label-holding pad.

(1-8-2) Production of Immunochromatographic Kit of Example 2

An immunochromatographic kit of Example 2 was produced in the same manner except for the fact that, in the production of the immunochromatographic kit of Example 1, the film-like fixation member fixing the gold colloid antibody-holding pad was installed so as to be visible from the pore for dropwise addition of specimen liquid (refer to FIG. 3B).

(1-8-3) Production of Immunochromatographic Kit of Comparative Example 1

A chromatographic carrier was produced in the same manner as the description of (1-3) except for the fact that, in the production of the chromatographic carrier of (1-3), the gold colloid antibody-holding pad was not fixed to the insoluble carrier with the enclosing film, that is, the gold colloid antibody-holding pad was not fixed to the insoluble carrier, and an immunochromatographic kit of Comparative Example 1 was produced in the same manner as in Example 1 except for the above-described fact.

(1-8-4) Production of Immunochromatographic Kit of Comparative Example 2

A chromatographic carrier was produced in the same manner as the description of (1-3) except for the fact that, in the production of the chromatographic carrier of (1-3), the amplification index region (coloring reagent immobilization line) was not provided, and an immunochromatographic kit of Comparative Example 2 was produced in the same manner as in Example 1 except for the above-described fact.

(2) Evaluation (2-1) Attachment in Scattered Manner

A liquid was produced by diluting a simulated cationic test body (BD Flu examine control A+B (manufactured by Becton, Dickinson and Company)) using an extraction liquid (1 mass % BIGCHAP-containing 1% BSA-PBS) 2,560 times, and 40 μL of the liquid was attached in a scattered manner to the anti-influenza A-type antibody-modified gold colloid-holding pad.

(2-2) Spreading of First Amplification Liquid (Reducing Agent Solution)

Immediately after the attachment of the specimen liquid in a scattered manner in (2-1), the first movable member was pressed down, the liquid-sending pad was displaced, and the liquid-sending pad was pressed into the first pot, thereby breaking the aluminium foil enclosing the first amplification liquid. The liquid-sending pad was immersed in the first pot, thereby supplying the first amplification liquid to the chromatographic carrier using the capillary action.

(2-3) Silver Amplification

After the amplification index region $L_3$ discolored to orange from the edge, the second movable member 24 was pressed down, and the second pot was moved toward the protrusion portion in the pot accommodation portion in the middle member 30, thereby breaking the aluminium foil enclosing the second amplification liquid in the second pot with the protrusion portion. The silver ion solution was supplied to the chromatographic carrier through a silver ion solution-filling hole in the middle member 30, thereby causing a silver amplification reaction.

Meanwhile, in Comparative Example 2, after five to ten minutes from the beginning of the sending of the first amplification liquid, the second movable member 24 was pressed down, and the second pot was moved toward the protrusion portion in the pot accommodation portion in the middle member 30, thereby breaking the aluminium foil enclosing the second amplification liquid in the second pot with the protrusion portion. The silver ion solution was supplied to the chromatographic carrier through a silver ion solution-filling hole in the middle member 30, thereby causing a silver amplification reaction.

(2-4) Computation of Amplification Success Percentage

The immunochromatographic kits of the respective examples and the respective comparative examples were prepared, the treatments described in (2-1), (2-2), and (2-3) were carried out ten times, and amplification success percentages were computed. When black lines were observed in the inspection region $L_1$ and the confirmation region $L_2$, amplification was determined as success.

(2-5) Computation of Concentration Value of Inspection Region

In order to confirm repetitive reproducibility, the chromatographic carriers were removed from the immunochromatographic kits of the respective examples and the respective comparative examples which had been subjected to the amplification treatment, the concentrations of the inspection regions $L_1$ were captured using LAS4000 (manufactured by Fujifilm Corporation), and the concentration difference ($\Delta$= (the concentration of the inspection region $L_1$)−(the concentration of the background portion)) was computed. In addition, for the respective examples and the respective comparative examples, the variations of concentration difference of ten times (N=10) were obtained.

Differences and evaluation results of the respective examples and the respective comparative examples are summarized in Table 1.

TABLE 1

| | Method for fixing label-holding pad | Presence or absence of amplification index region $L_3$ | Visibility of film-like fixation member from opening portion | Silver amplification success percentage | Concentration difference variation (CV) of N = 10 |
| --- | --- | --- | --- | --- | --- |
| Example 1 | Fixing two sides with film-like fixation member | Present | Not visible | 100% | 9.7% |
| Example 2 | Same as above | Present | Visible | 100% | 12.8% |
| Comparative Example 1 | Not fixed | Present | Not visible | 100% | 17.8% |
| Comparative Example 2 | Fixing two sides with film-like fixation member | Absent | Not visible | 50% | 105.5% |

It was found that, when the label-holding pad is fixed to the insoluble carrier, and the amplification index region is provided in the insoluble carrier, the success percentages of silver amplification reactions increases, the coefficient of variation (CV) in ten times of repetition of the same inspection is favorable, and the measurement accuracy is high. Furthermore, it became clear that, when the enclosing film fixing the gold colloid antibody-holding pad is disposed invisible from the pore for dropwise addition of specimen liquid, and only the region of the label-holding pad which is not covered with the enclosing film is set to be visible from the pore for dropwise addition of specimen liquid, the coefficient of variation (CV) further decreases, and it becomes possible to improve reproducibility.

In a case in which the gold colloid-holding pad was not fixed to the insoluble carrier, there were cases in which the pad was misaligned and the concentration of the gold colloid spreading in the width direction of the insoluble carrier became uneven, the measured concentration varied, and a decrease in CV was observed. In a case in which the amplification index region (coloring reagent immobilization line) was not provided, the timing of supplying the silver ion solution became unstable, the possibility of the failure of intended amplification increased, and the detection accuracy became low. From these results, the effects of the present invention were confirmed.

Next, examples and comparative examples of a second invention (Examples 11 and 20 and Comparative Example 1 to 4) will be described.

(21) Method for Producing Immunochromatographic Kits

The method for producing immunochromatographic kits is almost the same as the method for producing the immunochromatographic kit (1), and only differences from the method for producing (1) will be described.

In the production of the chromatographic carrier (1-3), a nitrocellulose membrane (with a plastic backing, HiFlow Plus HF135 (capillary flow rate=135 seconds/cm), manufactured by EMD Millipore Corporation) was used instead of the nitrocellulose membrane (with a plastic backing, HiFlow Plus HF120, manufactured by EMD Millipore Corporation).

In the production of the inspection strip (1-4), regarding the location of the label-holding pad 3 on the insoluble carrier 2, the distance B between the upstream end 3a of the label-holding pad 3 and the downstream end 4b of the liquid-sending pad 4 was set to become 12 mm.

(21-8-1) Production of Immunochromatographic Kit of Example 11

The lower case 10, the inspection strip produced in (1-4), and the absorption pad 5 produced in (1-6) were fixed as illustrated in FIG. 4. Next, the first pot 40 and the second pot 50 were respectively filled with the first amplification liquid 41 and the second amplification liquid 51 produced in (1-5-1) and (1-5-2), were enclosed with aluminium foils as the sheet member, and were mounted in the lower case 10 and the middle member 30 respectively as illustrated in FIG. 4. The first movable member 22 and the second movable member 24 were mounted in the upper case 20 through the insertion openings 23 and 25 respectively, and the lower case 10, the middle member 30, and the upper case 20 were assembled together as illustrated in FIG. 4, thereby producing an immunochromatographic kit.

In the present example 11, the distance A between the upstream end 2a of the insoluble carrier 2 and the upstream end 5a of the absorption pad 5 was set to 54 mm, and the distance B between the downstream end 3b of the label-holding pad 3 and the upstream end 64 of the surface 62 of the flow path-forming member 65 was set to 3 mm.

(21-8-2) Production of Immunochromatographic Kits of Examples 12 to 14 and Comparative Examples 11 to 13

Immunochromatographic kits of Examples 12 to 14 and Comparative Examples 11 to 13 were produced using the same constitution and order as in Example 11 except for the fact that, in the immunochromatographic kit of Example 11 described above, the distances A between the upstream end 2a of the insoluble carrier 2 and the upstream end 5a of the absorption pad 5 were changed, and absorption pads 5 having a different water absorption force were used as shown in Table 1 below.

(21-8-3) Production of Immunochromatographic Kits of Examples 15 and 16 and Comparative Example 14

Immunochromatographic kits of Examples 15 and 16 and Comparative Example 14 were produced using the same constitution and order as in Example 11 except for the fact that, in the step (1-4) of the method for producing the immunochromatographic kit of Example 11 described above, the locations on the insoluble carrier 2 to which the label-holding pad 3 was fixed were adjusted, and the distances B between the downstream end 3b of the label-holding pad 3 and the upstream end 64 of the surface 62 of the flow path-forming member 65 were changed as shown in Table 1 below.

(21-8-4) Production of Immunochromatographic Kit of Example 17

An immunochromatographic kit of Example 17 was produced using the same constitution and order as in Example 14 except for the fact that, in the step (1-4) of the method for producing the immunochromatographic kit of Example 14 described above, the location on the insoluble carrier 2 to which the label-holding pad 3 was fixed was adjusted, and the distance B between the downstream end 3b of the label-holding pad 3 and the upstream end 64 of the surface 62 of the flow path-forming member 65 was changed as shown in Table 1 below.

(21-8-5) Production of Immunochromatographic Kits of Examples 18 to 20

Immunochromatographic kits of Examples 18 and 19 were produced using the same constitution and order as in Example 1 except for the fact that, in the step (1-4) of the method for producing the immunochromatographic kit of Example 11 described above, the locations to which the liquid-sending pad 4 was attached were adjusted, and the distances C between the upstream end 3a of the label-holding pad 3 and the downstream end 4b of the liquid-sending pad 4 were changed. Regarding the distance C, the distances were set to 10 mm in Example 18, 18 mm in Example 19, and 30 mm in Example 20 respectively.

(22) Evaluation (22-1) Attachment in Scattered Manner

A liquid was produced by diluting a simulated cationic test body (BD Flu examine control A+B (manufactured by Becton, Dickinson and Company)) using an extraction liquid (1 mass % BIGCHAP-containing 1% BSA-PBS) 2,560 times, and 40 μL of the liquid was attached in a scattered manner to the anti-influenza A-type antibody-modified gold colloid-holding pad.

(22-2) Spreading of First Amplification Liquid (Reducing Agent Solution)

Immediately after the attachment of the specimen liquid in a scattered manner in (22-1), the first movable member 22 was pressed down, the liquid-sending pad 4 was displaced, and the liquid-sending pad 4 was pressed into the first pot 40, thereby breaking the aluminium foil enclosing the first amplification liquid 41. The liquid-sending pad 4 was immersed in the first pot 40, thereby supplying the first amplification liquid 41 to the chromatographic carrier using the capillary action.

(22-3) Measurement of Color Production Time

Immediately after the supply of the first amplification liquid 41 to the chromatographic carrier in (22-2), the time taken for the amplification index region $L_3$ to discolour from green to orange was measured as the color production time.

(22-4) Amplification Method

After the discoloration of the amplification index region $L_3$ from green to orange, the second movable member 24 was pressed down, and the second pot 50 was moved toward the protrusion portion 33 in the pot accommodation portion 32 in the middle member 30, thereby breaking the aluminium foil enclosing the second amplification liquid 51 in the second pot 50 with the protrusion portion 33. The silver ion solution that is the second amplification liquid 51 was supplied to the chromatographic carrier through the amplification liquid-filling hole 34 in the middle member 30, thereby causing a silver amplification reaction.

The second amplification liquid 51 added dropwise from the amplification liquid-filling hole 34 fills the gap 60 between the surface 62 of the flow path-forming member 65 and the insoluble carrier 2, is guided to the inspection region $L_1$ due to the capillary action, and the silver amplification reaction completes in several tens of seconds.

(22-5) Computation of Concentration Value of Inspection Region

The chromatographic carriers were removed from the immunochromatographic kits of the respective examples and the respective comparative examples which had been subjected to the amplification treatment, the concentrations of the inspection regions $L_1$ were captured using LAS4000 (manufactured by Fujifilm Corporation), and the concentration difference (ΔOD=(the concentration of the inspection region $L_1$)−(the concentration of the background portion)) was computed. Regarding the standard of the color production time, in consideration of inspection times suitable for POCT, 15 minutes or shorter was set as a preferred range.

is the amount of the weight increased before and after the placement of the absorption pad on the membrane was computed, and the amount of water absorbed per minute was obtained as the amount of water absorbed by the absorption pad.

(22-7) Evaluation of Concentration Unevenness

Regarding the concentration unevenness, sensory evaluation was carried out. The references of the evaluation were set as described below.

A: Concentration unevenness is not caused.

B: Slight concentration unevenness is caused, but is not sensed.

C: Concentration unevenness is caused and is not practically permitted.

Regarding the immunochromatographic kits of Examples 11 to 17 and Comparative Examples 11 to 14, constitutional differences and the above-described evaluation results are summarized in Table 2 below. Meanwhile, in all of the examples and the comparative examples, the distance D of the gap 60 being formed between the surface 62 of the flow path-forming member 65 and the surface 2S of the insoluble carrier 2 was set to 0.3 mm.

TABLE 2

| | Distance A between upstream end of insoluble carrier and upstream end of absorption pad (mm) | Water absorption force of absorption pad (μL/min.) | Distance B between downstream end of label-holding pad and upstream end of surface of flow path-forming member (mm) | Color production time (min.) | Concentration difference (ΔOD) | Evaluation of concentration unevenness | Note |
|---|---|---|---|---|---|---|---|
| Example 11 | 54 | 73 | 3 | 10 | 0.051 | A | |
| Example 12 | 54 | 45 | 3 | 12.6 | 0.051 | A | |
| Example 13 | 44 | 73 | 3 | 7.5 | 0.035 | A | |
| Example 14 | 64 | 73 | 3 | 13.2 | 0.065 | A | |
| Comparative Example 11 | 54 | 13 | 3 | 20.1 | 0.02 | A | |
| Comparative Example 12 | 54 | 5 | 3 | 52.7 | 0.01 | A | |
| Comparative Example 13 | 74 | 73 | 3 | — | 0 | A | The diffusion of the first amplification liquid stops in the middle. |
| Comparative Example 14 | 54 | 73 | 0.8 | 10 | 0.01 | C | |
| Example 15 | 54 | 73 | 1 | 10 | 0.051 | A | |
| Example 16 | 54 | 73 | 10 | 11.2 | 0.053 | A | |
| Example 17 | 64 | 73 | 19 | 12.4 | 0.052 | A | |

(22-6) Method for Measuring Water Absorption Force of Absorption Pad

In the present specification, the water absorption force of the absorption pad is defined as the amount of water absorbed per minute and is specifically obtained in the following manner.

A membrane of HiFlow Plus HF135 (capillary flow rate: 135 seconds/cm, manufactured by EMD Millipore Corporation) was cut to dimensions of 20 mm×20 mm and was caused to absorb a saturation amount of water. The absorption pad having dimensions of 15 mm×10 mm×2 mm was placed on the membrane, and a 630-gram weight having a bottom area of 20 mm×20 mm was placed thereon, and the absorption pad was pressed for ten seconds in this state. After ten seconds, the absorption pad was collected, and the weight was measured. The amount of water absorbed which From the results of Table 2, it is clear that, when the water absorption force of the absorption pad 5 was 45 μL/minute or more, and the distance A between the upstream end 2a of the insoluble carrier 2 and the upstream end 5a of the absorption pad 5 was 44 mm to 64 mm, the color production time was suppressed to 15 minutes or shorter, and favorable inspection could be carried out without concentration unevenness. When the water absorption force was less than 45 μL/minute as in Comparative Examples 11 and 12, the color production time became longer than 20 minutes, which is a result suitable for POCT. When the distance A was too long as in Comparative Example 13, the diffusion of the first amplification liquid stopped in the middle, and color was not produced. In addition, in a case in which the distance B between the upstream end 64 of the surface 62 of the flow path-forming member 65 and the downstream end 3b of the label-holding pad 3 was less than 1.0 mm as in Comparative Example 4, when the specimen liquid was attached to the label-holding pad 3 in a scattered manner, the specimen liquid entered the gap 60 between the flow path-forming member 65 and the insoluble carrier 2 due to the capillary action, and concentration unevenness was caused. That is, it became clear that the distance B between the downstream end 3b of the label-holding pad 3 and the upstream end 64 of the surface 62 of the flow path-forming member 65 needs to be set to 1.0 mm or more.

Furthermore, regarding Examples 11 and 18 to 20, constitutional differences and the above-described evaluation results are summarized in Table 3.

TABLE 3

|  | Distance C between upstream end of label-holding pad and downstream end of liquid-sending pad (mm) | Water absorption force of absorption pad (µL/min.) | Distance between downstream end of label-holding pad and upstream end of surface of flow path-forming member (mm) | Color production time (min.) | Concentration difference (ΔOD) | Evaluation of concentration unevenness |
|---|---|---|---|---|---|---|
| Example 11 | 12 | 73 | 3 | 10 | 0.051 | A |
| Example 18 | 11 | 73 | 3 | 10 | 0.041 | B |
| Example 19 | 18 | 73 | 3 | 10 | 0.051 | A |
| Example 20 | 30 | 73 | 3 | 10 | 0.051 | A |

From the results of Table 3, it was found that the distance C between the upstream end 3a of the label-holding pad 3 and the downstream end 4b of the liquid-sending pad 4 is desirably 12 mm or more. In a case in which the distance C is less than 12 mm as in Example 18, the fraction of the specimen liquid and the first amplification liquid being mixed together in a liquid phase increased, and there were cases in which unevenness of amplification (concentration unevenness) was caused.

EXPLANATION OF REFERENCES

1: inspection strip
2: insoluble carrier
2a: one end (upstream end) of insoluble carrier
3: label-holding pad
3a: upstream end of label-holding pad
3b: downstream end of label-holding pad
4: liquid-sending pad
4b: downstream end of liquid-sending pad
5: absorption pad
5a: upstream end of absorption pad
6: enclosing film (film-like fixation member)
7: back pressure-sensitive adhesion sheet
9: housing case
10: lower case
12: first pot accommodation portion
11, 13: accommodation portion of first pot
20: upper case
21: pore for dropwise addition of specimen liquid
22: first movable member
23: insertion opening of first movable member
24: second movable member
25: insertion opening of second movable member
30: middle member
32: accommodation portion of second pot
33: protrusion portion
34: amplification liquid-filling hole
40: first pot for first amplification liquid
41: first amplification liquid
50: second pot for second amplification liquid
51: second amplification liquid
60: gap
61: observation window
62: surface of flow path-forming member
64: upstream end of flow path-forming member
65: flow path-forming member
100: immunochromatographic kit
$L_1$: inspection region
$L_2$: confirmation region
$L_3$: amplification index region

What is claimed is:

1. An immunochromatographic kit detecting a test substance in a specimen liquid, comprising:
an inspection strip that includes an insoluble carrier spreading the specimen liquid, a label-holding pad including a label substance modified with a first substance bondable to the test substance fixed on the insoluble carrier, a liquid-sending pad in contact with one end of the insoluble carrier and sending a first amplification liquid to the insoluble carrier, and an absorption pad in contact with another end of the insoluble carrier, and the inspection strip sequentially having an inspection region including a second substance bonded to the test substance, a confirmation region including a substance bondable to the first substance, and an amplification index region including a substance that reacts with the first amplification liquid, from a label-holding pad side between the label-holding pad and the absorption pad of the insoluble carrier;
a first pot disposed below the liquid-sending pad and enclosing the first amplification liquid;
a second pot disposed above the absorption pad and enclosing a second amplification liquid; and
a housing case containing the inspection strip, the first pot, and the second pot and having a pore for dropwise addition of the specimen liquid facing the label-holding pad,
wherein the first pot has one surface including a sheet member,
wherein the surface including the sheet member of the first pot is disposed against the liquid-sending pad,
wherein a movable member is disposed at a location facing the sheet member of the first pot through the liquid-sending pad and presses and displaces the liquid-sending pad in response to an external pressing force to break the sheet member of the first pot and press the liquid-sending pad into the first pot, and
wherein the immunochromatographic kit further comprises a movement prevention mechanism restricting movement of the movable member toward an original position side after pressing the liquid-sending pad into the first pot.

2. The immunochromatographic kit according to claim 1, wherein:
the housing case includes an upper case having the pore for dropwise addition of the specimen liquid, a lower case having an accommodation portion in which the inspection strip is disposed, and a middle member disposed between the upper case and the lower case, and
the middle member has a pot accommodation portion that accommodates the second pot and includes a hole for causing the second amplification liquid to flow down, in a bottom surface thereof.

3. The immunochromatographic kit according to claim 1, wherein the second pot has one surface including a sheet member.

4. The immunochromatographic kit according to claim 1, wherein:
the housing case includes an upper case having the pore for dropwise addition of the specimen liquid, a lower case having an accommodation portion in which the inspection strip is disposed, and a middle member disposed between the upper case and the lower case,
the middle member has a pot accommodation portion that accommodates the second pot and includes a hole for causing the second amplification liquid to flow down, in a bottom surface thereof,
the second pot has one surface including a sheet member,
a protrusion portion breaking the sheet member of the second pot is provided in the pot accommodation portion of the middle member against the sheet member of the second pot, and
the immunochromatographic kit is provided with a movable member relatively moving the second pot with respect to the protrusion portion to a location at which the sheet member is broken by the protrusion portion.

5. The immunochromatographic kit according to claim 1, wherein:
at least two sides of the label-holding pad are covered with a film-like fixation member and are fixed to the insoluble carrier, and
a region of the label-holding pad facing the pore for dropwise addition of the specimen liquid of the housing case is not covered with the film-like fixation member.

6. The immunochromatographic kit according to claim 1, wherein:
the first amplification liquid is a reducing agent liquid for silver ions, and
the second amplification liquid is a solution including silver ions.

7. The immunochromatographic kit according to claim 1, wherein the first amplification liquid is a solution including divalent iron ions.

8. The immunochromatographic kit according to claim 1, wherein a substance reacted with the first amplification liquid is a substance reacted through protons.

9. The immunochromatographic kit according to claim 1, wherein the label substance is a metal colloid.

10. An immunochromatographic kit detecting a test substance in a specimen liquid, comprising:
an inspection strip that includes an insoluble carrier spreading the specimen liquid, a label-holding pad including a label substance modified with a first substance bondable to the test substance fixed on the insoluble carrier, a liquid-sending pad in contact with one end of the insoluble carrier and sending a first amplification liquid to the insoluble carrier, and an absorption pad in contact with another end of the insoluble carrier, and the inspection strip having an inspection region including a second substance bonded to the test substance between the label-holding pad and the absorption pad of the insoluble carrier;
a first pot disposed below the liquid-sending pad and enclosing the first amplification liquid;
a second pot disposed above the absorption pad and enclosing a second amplification liquid; and
a housing case containing the inspection strip, the first pot, and the second pot,
wherein the housing case comprises a lower case including an accommodation portion in which the inspection strip is disposed, an upper case fitted with the lower case, and a flow path-forming member disposed between the upper case and the lower case,
wherein the flow path-forming member has one surface forming a gap that guides the second amplification liquid, which is added dropwise onto the insoluble carrier, onto the inspection region, between a surface of the insoluble carrier and the flow path-forming member,
wherein a water absorption force of the absorption pad is from 45 µL/minute to 90 µL/minute,
wherein, in a case in which a liquid-sending pad side is designated as upstream and an absorption pad side is designated as downstream in the inspection strip, a distance between the one end of the insoluble carrier and an upstream-side end of the absorption pad is from 44 mm to 64 mm,
wherein a distance between an upstream-side end of the surface of the flow path-forming member and a downstream-side end of the label-holding pad is from 1 mm to 19 mm,
wherein the first pot has one surface including a sheet member,
wherein the surface including the sheet member of the first pot is disposed against the liquid-sending pad,
wherein a movable member is disposed at a location facing the sheet member of the first pot through the liquid-sending pad and presses and displaces the liquid-sending pad in response to an external pressing force to break the sheet member of the first pot and press the liquid-sending pad into the first pot, and
wherein the immunochromatographic kit is provided with a movement prevention mechanism restricting movement of the movable member toward an original position side after pressing the liquid-sending pad into the first pot.

11. The immunochromatographic kit according to claim 10, wherein the gap is from 0.01 mm to 1.00 mm.

12. The immunochromatographic kit according to claim 10, wherein a distance between an upstream-side end of the label-holding pad and a downstream-side end of the liquid-sending pad is from 12 mm to 30 mm.

13. The immunochromatographic kit according to claim 10, wherein a distance between the one end of the insoluble carrier and the upstream-side end of the absorption pad is from 49 mm to 59 mm.

14. The immunochromatographic kit according to claim 10, wherein the water absorption force of the absorption pad is from 65 µL/minute to 75 µL/minute.

15. The immunochromatographic kit according to claim 10, wherein a confirmation region including a substance bondable to the first substance and an amplification index region including a substance that reacts with the first amplification liquid are sequentially provided from an inspection region side between the inspection region on the insoluble carrier and the absorption pad.

16. The immunochromatographic kit according to claim 15, wherein a substance reacted with the first amplification liquid is a substance reacted through protons.

17. The immunochromatographic kit according to claim 10, wherein:
the immunochromatographic kit is provided with a middle member disposed between the upper case and the lower case, and
the middle member has a pot accommodation portion that accommodates the second pot and includes a hole for adding the second amplification liquid dropwise onto the insoluble carrier, in a bottom surface thereof.

18. The immunochromatographic kit according to claim 17, wherein the middle member is integrally formed with the flow path-forming member.

19. The immunochromatographic kit according to claim 10, wherein the second amplification liquid is added dropwise on the downstream side of the inspection region in the insoluble carrier.

20. The immunochromatographic kit according to claim 10, wherein:
the first amplification liquid is a reducing agent liquid for silver ions, and
the second amplification liquid is a solution including silver ions.

21. The immunochromatographic kit according to claim 10, wherein the first amplification liquid is a solution including divalent iron ions.

22. The immunochromatographic kit according to claim 10, wherein the label substance is a metal colloid.

* * * * *